(12) United States Patent
Penake et al.

(10) Patent No.: US 10,434,248 B1
(45) Date of Patent: Oct. 8, 2019

(54) KIT AND METHOD OF REDUCING HUMAN ERROR DURING IMPLANTED INFUSION PUMP REFILLING

(71) Applicant: SAOL INTERNATIONAL LIMITED, Hamilton (BM)

(72) Inventors: David Allen Penake, Atlanta, GA (US); Sharon Hamm, Odessa, FL (US); Martin Reynell, Dublin (IE)

(73) Assignee: Saol International Limited, Hamilton (BM)

( * ) Notice: Subject to any disclaimer, the term of this patent is extended or adjusted under 35 U.S.C. 154(b) by 0 days.

(21) Appl. No.: 15/935,894

(22) Filed: Mar. 26, 2018

(51) Int. Cl.
*A61M 5/42* (2006.01)
*A61M 39/02* (2006.01)
*A61M 5/142* (2006.01)

(52) U.S. Cl.
CPC ........ *A61M 5/14276* (2013.01); *A61M 5/427* (2013.01); *A61M 39/0208* (2013.01); *A61M 2005/14284* (2013.01); *A61M 2039/0238* (2013.01)

(58) Field of Classification Search
CPC .......... A61M 5/14532; A61M 5/14276; A61M 5/427; A61M 39/0208
See application file for complete search history.

(56) References Cited

U.S. PATENT DOCUMENTS

| | | | |
|---|---|---|---|
| 3,438,737 A * | 4/1969 | Fader ................. | G01N 33/6839 422/401 |
| 4,573,994 A * | 3/1986 | Fischell ............ | A61M 5/14276 604/140 |
| 4,820,297 A | 4/1989 | Kaufman | |
| 5,569,186 A * | 10/1996 | Lord ..................... | A61B 5/0002 604/67 |
| 7,044,932 B2 | 5/2006 | Borchard | |
| 9,227,048 B2 | 1/2016 | Gobbi Frattini | |
| 2004/0127816 A1 | 7/2004 | Galvo | |
| 2008/0294148 A1 | 11/2008 | Gardner | |
| 2009/0198182 A1 | 8/2009 | Fujishima | |
| 2011/0054353 A1 | 3/2011 | Hulvershorn | |
| 2013/0116666 A1 | 5/2013 | Minipumps | |
| 2015/0112248 A1 | 8/2015 | Accuro | |
| 2016/0220161 A1 | 8/2016 | Smith Med | |

FOREIGN PATENT DOCUMENTS

| | | |
|---|---|---|
| WO | 2003/043496 | 5/2003 |
| WO | 2006/007711 | 1/2006 |

OTHER PUBLICATIONS

Two page document describing a Huber needle and a Bard port.
Article in Pain Medicine 2011 by M. Gofled entitled Ultrasound-Guided Intrathecal Pump Access and Prevention of the Pocket Fill.
PCT Search Report issued in PCT/US19/23891(15 pages).
Article entitled Determination of Serum Proteins by Means of the Biuret Reaction by A. G. Gornall et al.

* cited by examiner

*Primary Examiner* — Nathan R Price
*Assistant Examiner* — Tasnim Mehjabin Ahmed
(74) *Attorney, Agent, or Firm* — Greenblum & Bernstein, P.L.C.

(57) ABSTRACT

Protein detection kit usable with implanted infusion pumps. The kit includes at least one container containing a protein-detecting composition and having an interface for allowing fluid to be introduced and a visual indicating mechanism for providing a visual indicator indicative of protein detection.

3 Claims, 29 Drawing Sheets

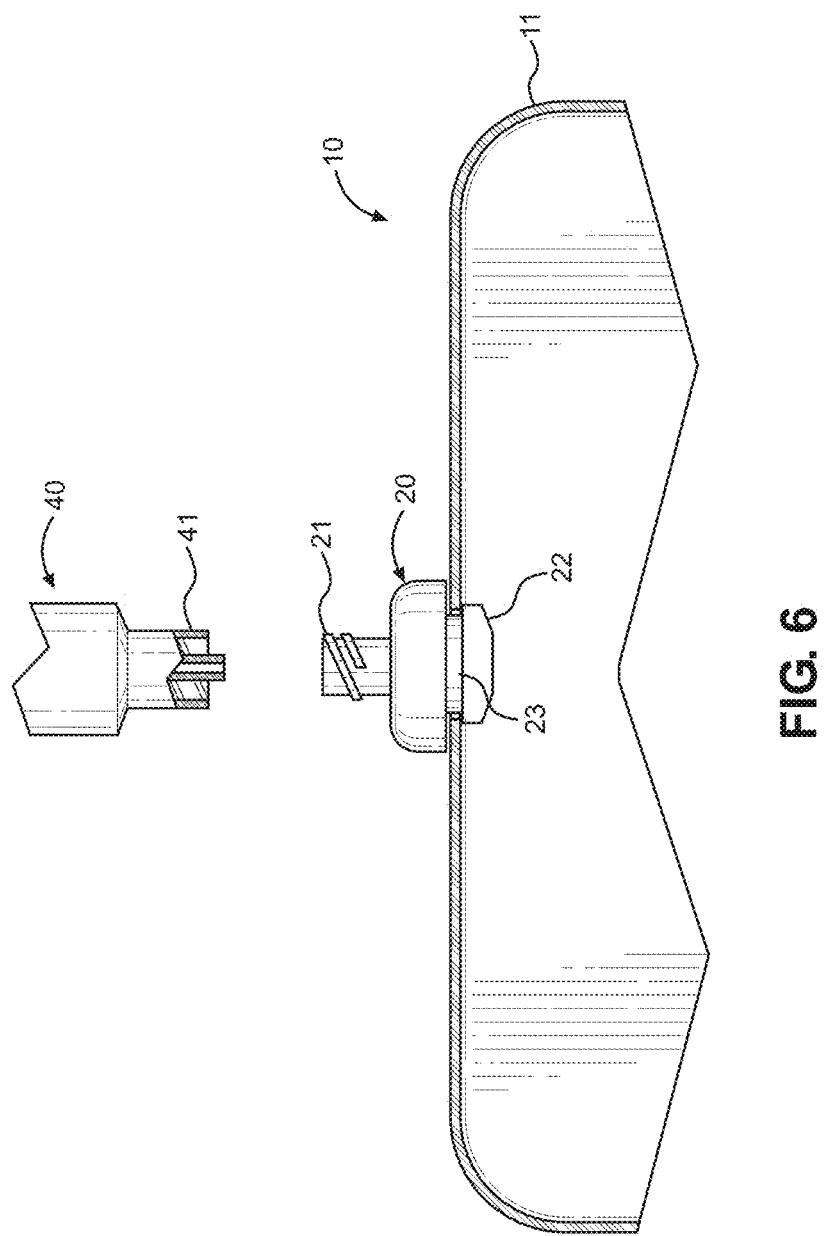

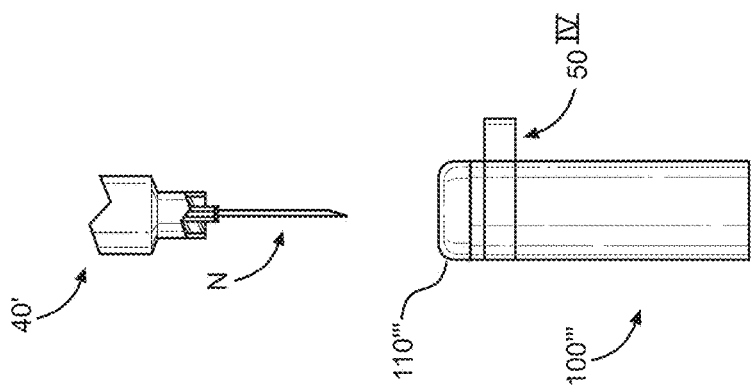
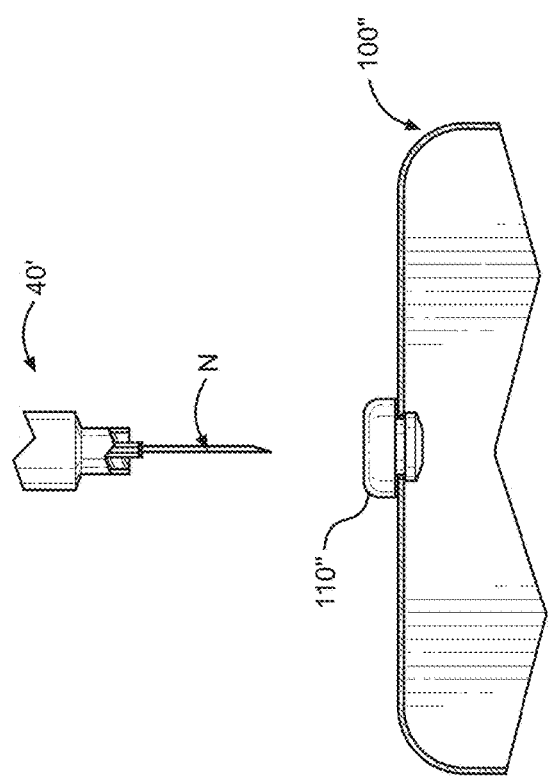

| Material | | Item number | Lot number |
|---|---|---|---|
| Copper (II) Sulfate Pentahydrate | MW: 249,69g/mol | NA | #01239 |
| Potassium Sodium Tartrate Tetrahydrate | MW: 282,22g/mol | NA | #01238 |
| Sodium Hydroxide | MW: 40,00g/mol | 10-0032 | #00037 |
| Potassium Iodide | MW: 166,00g/mol | NA | #01237 |
| Distilled water | | 10-0012 | #01155 |

| Instrument | Item number |
|---|---|
| Analytical Balance | BA-03 |

Preparation of solutions:

1. Volume to be prepared is: 100 mL

2. Take an appropriate container and add the following components successively and quantitatively into the container. Mix until all components are dissolved.

| | QTY/Liter | Qty Required | Qty used | |
|---|---|---|---|---|
| Distilled water | 400 mL | 40.0 | 40.0 | mL |
| Copper (II) Sulfate pentahydrate | 1.50 g | 0.15 | 0.1505 | g |
| Potassium Sodium Tartrate | 6.00 g | 0.60 | 0.6002 | g |

3. Adjust the volume of the solution to half of the final volume with distilled water.
   volume adjusted to: 50.0 mL

| | QTY/Liter | Qty Required | |
|---|---|---|---|
| 4. Make a 10% (w/v) Sodium Hydroxide solution | 300 mL | 30.0 | mL |
| Sodium Hydroxide (Qty Required /10) | | Qty used: 3.019 | g |

5. Adjust the volume of the 10% (w/v) Sodium Hydroxide solution to the final volume with distilled water. 30.0 mL 6. Mix both solutions together and adjust the volume to the final volume with distilled water.
   volume adjusted to: 100 mL

| | QTY/Liter | Qty Required | Qty used | |
|---|---|---|---|---|
| 7. Add Potassium Iodide to the mixture | 1.00 g | 0.10 | 0.1043 | g |

8. Store the solution at RT (20-25°C) in a dark plastic container. Discard the buffer if any black or reddish precipitate is observed.

| Lot number: | #exp412PL-1 |
|---|---|
| Exp. date: | 15-Feb-18 |

FIG. 29

Materials:

| Material | | Item number | Lot number |
|---|---|---|---|
| Copper (II) Sulfate Pentahydrate | MW: 249.69g/mol | NA | #01239 |
| Potassium Sodium Tartrate Tetrahydrate | MW: 282.22g/mol | NA | #01238 |
| Sodium Hydroxide | MW: 40.00g/mol | 10-0032 | #00037 |
| Potassium Iodide | MW: 166.00g/mol | NA | #01237 |
| Distilled water | | 10-0012 | #01155 |

| Instrument | Item number |
|---|---|
| Analytical Balance | BA-03 |

Preparation of solution:

1. Volume to be prepared is [100] mL.

2. Take an appropriate container and add the following components successively and quantitatively into the container. Mix until all components are dissolved.

| | QTY/Liter | Qty Required | Qty used | |
|---|---|---|---|---|
| Distilled water | 700 mL | 70.0 | 70.0 | mL |
| Copper (II) Sulfate pentahydrate | 15.0 g | 1.5 | 1.5002 | g |
| Potassium Sodium Tartrate | 45.0 g | 4.50 | 4.5016 | g |

3. Adjust the volume of the solution to half of the final volume with distilled water.
   volume adjusted to: [70.0] mL 4. Make a 10% (w/v) Sodium Hydroxide solution.

| | QTY/Liter | Qty Required | |
|---|---|---|---|
| | 80.0 mL | 8.00 | mL |

| Sodium Hydroxide (Qty Required /10) | Qty produced | 50.0 | mL | Qty used | 5.0058 | g |

Produced 50mL of 10% (w/v) NaOH solution for future use.

Lot number: Rexp419PL-1
Exp. date: 1-Sep-18

5. Adjust the volume of the 10% (w/v) Sodium Hydroxide solution to the final volume with distilled water. [50.0] mL 6. Mix both solutions together and adjust the volume to the final volume with distilled water. (used 8mL of 10% (w/v) NaOH)

| | QTY/Liter | Qty Required | Qty used | |
|---|---|---|---|---|
| 7. Add Potassium Iodide to the mixture | 5.00 g | 0.50 | 0.5092 | g |

8. Store the solution at RT (20-25°C) in a dark plastic container. Discard the buffer if any black or reddish precipitate is observed.

Lot number: Rexp419PL-2
Exp. date: 1-Nov-18

FIG. 30

| Material | | Item number | Lot number |
|---|---|---|---|
| Copper (II) Sulfate Pentahydrate | MW: 249,69g/mol | NA | #01239 |
| Potassium Sodium Tartrate Tetrahydrate | MW: 282,22g/mol | NA | #01238 |
| 10% Sodium Hydroxide solution | | NA | #exp419PL-1 |
| Potassium Iodide | MW: 166,00g/mol | NA | #01237 |
| Distilled water | | 10-0012 | #01155 |
| Triton X-100 | | 10-0061 | #00141 |
| Weichselbaum biuret solution | | NA | #exp419PL-2 |
| Gornall Biuret solution | | NA | #exp412PL-1 |
| BSA Calibrator set | | NA | #exp424PL-2 |

1 Volume to be prepared is   100   mL

2 Take an appropriate container and add the following components successively and quantitatively into the container.
  Mix until all components are dissolved.

| | QTY/Liter | Qty Required | Qty used | |
|---|---|---|---|---|
| Distilled water | 700 mL | 70.0 | 70.0 | mL |
| Copper (II) Sulfate pentahydrate | 3,00 g | 0.30 | 0.3013 | g |
| Potassium Sodium Tartrate | 9,00 g | 0.90 | 0.9045 | g |
| 10% (w/v) Sodium Hydroxide | 80,0 mL | 8.00 | 8.00 | mL |

| | QTY/Liter | Qty Required | Qty used | |
|---|---|---|---|---|
| 3 Add Potassium Iodide to the mixture | 5,00 g | 0.50 | 0.4747 | g |
| Add Triton X-100 | 1,4 mL | 0.14 | 0.1400 | g |

4 Store the solution at RT (20-25°C) in a dark plastic container. Discard the buffer if any black or reddish precipitate is observed.

Lot number: #exp003MS-1
Exp. date: 13-Mar-18

FIG. 31

* Exp418PL: Testing Seracon II CD using the Gornall Biuret solution – determination of the protein concentration of Seracon – Seracon is charcoal stripped, delipidated human plasma.

| Material | | Item number | Lot number |
|---|---|---|---|
| Round bottom plate | | NA | NA |
| Probumin BSA diagnostic solution - 30% std | 333.33mg/mL | 10-0091 | 808986 |
| Seracon II CD | Total protein: 64g/dL | NA | 801152 |
| Sodium Chloride | | 10-0016 | 808999 |
| Distilled water | | 10-0012 | 801195 |
| Gornall Biuret solution | | NA | Exp412PL-1 |

| Sample | [mg/mL] | Start time: 1:22:23 | +1 min 1:23:40 | +1 min 1:24:40 | +3 min 1:27:41 | +5 min 1:32:34 | +5 min 1:37:39 | (15 minutes total) Mean OD | Conc. (mg/mL) | | |
|---|---|---|---|---|---|---|---|---|---|---|---|
| | | | | OD570nm | | | | | | | |
| Cal0 | 0.00 | 0.065 | 0.066 | 0.066 | 0.066 | 0.066 | 0.066 | 0.066 | -0.04 | | |
| Cal0.5 | 0.50 | 0.100 | 0.109 | 0.111 | 0.116 | 0.119 | 0.120 | 0.113 | 0.50 | | |
| Cal1 | 1.00 | 0.147 | 0.156 | 0.158 | 0.163 | 0.166 | 0.167 | 0.160 | 1.04 | | |
| Cal1.5 | 1.50 | 0.186 | 0.200 | 0.201 | 0.209 | 0.213 | 0.215 | 0.204 | 1.56 | | |
| Cal2 | 2.00 | 0.216 | 0.233 | 0.238 | 0.245 | 0.251 | 0.255 | 0.240 | 1.97 | | |
| Cal2.5 | 2.50 | 0.258 | 0.277 | 0.283 | 0.290 | 0.296 | 0.298 | 0.284 | 2.47 | | |
| Cal3 | 3.00 | 0.275 | 0.292 | 0.298 | 0.304 | 0.307 | 0.310 | 0.298 | 2.64 | | |
| Cal4 | 4.00 | 0.286 | 0.299 | 0.303 | 0.308 | 0.309 | 0.311 | 0.303 | 2.69 | | |
| Cal5 | 5.00 | 0.338 | 0.346 | 0.346 | 0.344 | 0.341 | 0.337 | 0.342 | 3.15 | | |
| Cal6 | 6.00 | 0.338 | 0.341 | 0.340 | 0.334 | 0.329 | 0.325 | 0.334 | 3.06 | | |
| Cal8 | 8.00 | 0.318 | 0.318 | 0.317 | 0.315 | 0.316 | 0.313 | 0.316 | 2.85 | | |
| Cal10 | 10.0 | 0.312 | 0.315 | 0.315 | 0.315 | 0.317 | 0.316 | 0.315 | 2.84 | | |
| Cal30 | 30.0 | 0.297 | 0.304 | 0.305 | 0.309 | 0.312 | 0.314 | 0.308 | 2.75 | | |
| Cal60 | 60.0 | 0.289 | 0.293 | 0.296 | 0.303 | 0.303 | 0.294 | 0.297 | 2.63 | Conc. x dil factor | Recovery% |
| Biuret | 0.00 | 0.069 | 0.071 | 0.071 | 0.072 | 0.070 | 0.069 | 0.070 | 0.01 | | |
| Serac neat | 64.0 | 0.289 | 0.293 | 0.293 | 0.301 | 0.313 | 0.321 | 0.301 | 2.68 | 2.68 | 4.19% |
| Serac 2x dil | 32.0 | 0.297 | 0.300 | 0.301 | 0.308 | 0.330 | 0.345 | 0.314 | 2.82 | 5.63 | 8.83% |
| Serac 4x dil | 16.0 | 0.294 | 0.295 | 0.296 | 0.304 | 0.317 | 0.317 | 0.304 | 2.71 | 10.8 | 16.9% |
| Serac 8x dil | 8.00 | 0.302 | 0.305 | 0.305 | 0.304 | 0.304 | 0.304 | 0.304 | 2.71 | 21.7 | 33.9% |
| Serac 16x dil | 4.00 | 0.318 | 0.322 | 0.322 | 0.327 | 0.320 | 0.316 | 0.319 | 2.88 | 46.2 | 72.1% |
| Serac 32x dil | 2.00 | 0.234 | 0.259 | 0.265 | 0.275 | 0.281 | 0.285 | 0.267 | 2.28 | 72.9 | 114% |
| Serac 64x dil | 1.00 | 0.161 | 0.175 | 0.180 | 0.185 | 0.189 | 0.191 | 0.180 | 1.28 | 81.9 | 128% |
| Serac 128x dil | 0.50 | 0.112 | 0.119 | 0.121 | 0.124 | 0.126 | 0.127 | 0.122 | 0.60 | 77.1 | 120% |
| Serac 256x dil | 0.25 | 0.089 | 0.094 | 0.095 | 0.097 | 0.097 | 0.098 | 0.095 | 0.30 | 75.9 | 119% |
| | | | | | | | | | Mean (32x-256x dil) | 76.9 | 120% |

| | Mean OD570nm 0.00 - 2.50mg/mL | | | | | | | |
|---|---|---|---|---|---|---|---|---|
| [mg/mL] | 0 | 1 | 1 | 1.5 | 2 | 3 | Slope | Intercept |
| OD | 0.066 | 0.113 | 0.160 | 0.204 | 0.240 | 0.284 | 0.087 | 0.0693 |

FIG. 32

| Weichselbaum Biuret solution | | | | | | | | | | |
|---|---|---|---|---|---|---|---|---|---|---|
| | Start | +1 min | +1 min | +1 min | +1 min | +1 min | +5 min | +5 min | +15 min | |
| time: | 0:39:38 | 0:40:44 | 0:41:49 | 0:42:56 | 0:44:01 | 0:45:07 | 0:50:13 | 0:55:12 | 1:10:17 | |
| [mg/ml] | | | | | OD570nm | | | | | Mean OD |
| 0.00 | 0.262 | 0.262 | 0.262 | 0.263 | 0.263 | 0.263 | 0.263 | 0.262 | 0.261 | 0.262 |
| 0.50 | 0.278 | 0.284 | 0.287 | 0.289 | 0.290 | 0.291 | 0.292 | 0.294 | 0.293 | 0.289 |
| 1.00 | 0.293 | 0.307 | 0.313 | 0.316 | 0.318 | 0.319 | 0.323 | 0.325 | 0.326 | 0.316 |
| 1.50 | 0.323 | 0.344 | 0.353 | 0.358 | 0.361 | 0.363 | 0.369 | 0.370 | 0.371 | 0.357 |
| 2.00 | 0.343 | 0.371 | 0.382 | 0.389 | 0.394 | 0.398 | 0.406 | 0.408 | 0.409 | 0.389 |
| 2.50 | 0.361 | 0.395 | 0.409 | 0.418 | 0.423 | 0.429 | 0.440 | 0.445 | 0.447 | 0.419 |
| 3.00 | 0.379 | 0.420 | 0.438 | 0.448 | 0.455 | 0.458 | 0.472 | 0.478 | 0.481 | 0.448 |
| 4.00 | 0.430 | 0.483 | 0.506 | 0.520 | 0.528 | 0.534 | 0.552 | 0.558 | 0.564 | 0.519 |
| 5.00 | 0.458 | 0.530 | 0.559 | 0.577 | 0.589 | 0.597 | 0.621 | 0.630 | 0.638 | 0.578 |
| 6.00 | 0.484 | 0.567 | 0.603 | 0.624 | 0.638 | 0.649 | 0.675 | 0.686 | 0.696 | 0.625 |
| 8.00 | 0.544 | 0.653 | 0.698 | 0.727 | 0.745 | 0.758 | 0.794 | 0.812 | 0.830 | 0.729 |
| 10.0 | 0.611 | 0.743 | 0.799 | 0.832 | 0.854 | 0.870 | 0.912 | 0.931 | 0.957 | 0.834 |
| 30.0 | 0.959 | 1.205 | 1.315 | 1.383 | 1.427 | 1.462 | 1.530 | 1.579 | 1.593 | 1.386 |
| 60.0 | 1.035 | 1.273 | 1.366 | 1.424 | 1.464 | 1.497 | 1.568 | 1.592 | 1.596 | 1.424 |
| W. Biuret | 0.470 | 0.470 | 0.470 | 0.470 | 0.470 | 0.470 | 0.471 | 0.472 | 0.473 | 0.471 |
| W. Biuret | 0.480 | 0.480 | 0.481 | 0.482 | 0.482 | 0.481 | 0.482 | 0.482 | 0.483 | 0.481 |

FIG. 34

| Gornall Biuret solution | | | | | | | | | | |
|---|---|---|---|---|---|---|---|---|---|---|
| | Start | +1 min | +1 min | +3 min | +5 min | +5 min | | | | |
| time: | 0:39:38 | 0:40:44 | 0:41:49 | 0:42:56 | 0:44:01 | 0:45:07 | 0:50:13 | 0:55:12 | 1:10:17 | |
| [mg/ml] | | | | | OD570nm | | | | | Mean OD |
| 0.00 | 0.065 | 0.066 | 0.066 | 0.066 | 0.066 | 0.066 | 0.066 | 0.066 | 0.065 | 0.065 |
| 0.50 | 0.103 | 0.109 | 0.110 | 0.111 | 0.112 | 0.113 | 0.115 | 0.116 | 0.117 | 0.112 |
| 1.00 | 0.138 | 0.150 | 0.154 | 0.156 | 0.157 | 0.158 | 0.161 | 0.163 | 0.165 | 0.156 |
| 1.50 | 0.177 | 0.193 | 0.199 | 0.203 | 0.204 | 0.205 | 0.210 | 0.211 | 0.216 | 0.202 |
| 2.00 | 0.210 | 0.232 | 0.240 | 0.244 | 0.247 | 0.249 | 0.254 | 0.255 | 0.258 | 0.243 |
| 2.50 | 0.244 | 0.270 | 0.278 | 0.282 | 0.285 | 0.287 | 0.293 | 0.296 | 0.303 | 0.282 |
| 3.00 | 0.266 | 0.292 | 0.299 | 0.302 | 0.303 | 0.305 | 0.309 | 0.311 | 0.318 | 0.301 |
| 4.00 | 0.294 | 0.314 | 0.319 | 0.320 | 0.321 | 0.322 | 0.323 | 0.321 | 0.321 | 0.317 |
| 5.00 | 0.304 | 0.321 | 0.326 | 0.328 | 0.330 | 0.330 | 0.333 | 0.332 | 0.317 | 0.325 |
| 6.00 | 0.298 | 0.315 | 0.319 | 0.321 | 0.322 | 0.324 | 0.327 | 0.325 | 0.307 | 0.318 |
| 8.00 | 0.299 | 0.313 | 0.317 | 0.319 | 0.319 | 0.318 | 0.316 | 0.311 | 0.304 | 0.313 |
| 10.0 | 0.306 | 0.317 | 0.323 | 0.325 | 0.324 | 0.322 | 0.315 | 0.313 | 0.313 | 0.318 |
| 30.0 | 0.303 | 0.317 | 0.313 | 0.312 | 0.311 | 0.312 | 0.318 | 0.316 | 0.280 | 0.309 |
| 60.0 | 0.316 | 0.311 | 0.310 | 0.309 | 0.309 | 0.310 | 0.313 | 0.294 | 0.223 | 0.299 |
| G. Biuret | 0.102 | 0.103 | 0.104 | 0.102 | 0.102 | 0.102 | 0.101 | 0.103 | 0.104 | 0.103 |
| G. Biuret | 0.101 | 0.103 | 0.104 | 0.102 | 0.102 | 0.101 | 0.101 | 0.103 | 0.102 | 0.102 |

FIG. 35

NBCL (VWR) biuret solution

| Sample | [mg/mL] | OD1 | OD2 | mean | STDEV | CV% |
|---|---|---|---|---|---|---|
| Cal0 | 0.00 | 0.088 | 0.088 | 0.088 | 0.00 | 0.00% |
| Cal1 | 0.00 | 0.087 | 0.087 | 0.087 | 0.00 | 0.00% |
| Cal2 | 1.00 | 0.142 | 0.153 | 0.148 | 0.01 | 5.27% |
| Cal3 | 3.00 | 0.323 | 0.328 | 0.326 | 0.00 | 1.09% |
| Cal4 | 6.00 | 0.545 | 0.520 | 0.533 | 0.02 | 3.32% |
| Cal5 | 10.0 | 0.706 | 0.713 | 0.710 | 0.00 | 0.70% |
| Cal6 | 30.0 | 0.583 | 0.567 | 0.575 | 0.01 | 1.97% |
| Cal7 | 60.0 | 0.531 | 0.537 | 0.534 | 0.00 | 0.79% |

Weichselbaum biuret solution

| Sample | [mg/mL] | OD1 | OD2 | mean | STDEV | CV% |
|---|---|---|---|---|---|---|
| Cal0 | 0.00 | 0.256 | 0.260 | 0.258 | 0.00 | 1.10% |
| Cal1 | 0.00 | 0.259 | 0.262 | 0.261 | 0.00 | 0.81% |
| Cal2 | 1.00 | 0.349 | 0.304 | 0.327 | 0.03 | 9.75% |
| Cal3 | 3.00 | 0.377 | 0.422 | 0.400 | 0.03 | 7.96% |
| Cal4 | 6.00 | 0.481 | 0.579 | 0.530 | 0.07 | 13.1% |
| Cal5 | 10.0 | 0.726 | 0.802 | 0.764 | 0.05 | 7.03% |
| Cal6 | 30.0 | 1.249 | 1.070 | 1.160 | 0.13 | 10.9% |
| Cal7 | 60.0 | 1.255 | 1.334 | 1.295 | 0.06 | 4.32% |

Gornall biuret solution

| Sample | [mg/mL] | OD1 | OD2 | mean | STDEV | CV% |
|---|---|---|---|---|---|---|
| Cal0 | 0.00 | 0.068 | 0.070 | 0.070 | 0.00 | 2.02% |
| Cal1 | 0.00 | 0.064 | 0.065 | 0.065 | 0.00 | 1.10% |
| Cal2 | 1.00 | 0.120 | 0.113 | 0.117 | 0.00 | 4.25% |
| Cal3 | 3.00 | 0.230 | 0.215 | 0.223 | 0.01 | 4.77% |
| Cal4 | 6.00 | 0.267 | 0.283 | 0.275 | 0.01 | 4.11% |
| Cal5 | 10.0 | 0.280 | 0.304 | 0.292 | 0.02 | 5.81% |
| Cal6 | 30.0 | 0.325 | 0.305 | 0.315 | 0.01 | 4.49% |
| Cal7 | 60.0 | 0.280 | 0.289 | 0.285 | 0.01 | 2.24% |

*Modified biuret solution*

FIG. 37

| Material | | | | | | Item number | Lot number |
|---|---|---|---|---|---|---|---|
| Round bottom plate | | | | | | NA | NA |
| Prebovine BSA calibration curve | | | | | | NA | dexp006MS-2 |
| Saline | | | | | 0.9% NaCl solution | NA | dexp006MS-1 |
| Work biuret reagent | | | | | | NA | 401376 |

| Overview OD | BSA [mg/mL] | | | | | | |
|---|---|---|---|---|---|---|---|
| ratio BSA/Biuret | 0.00 | 1.00 | 3.00 | 6.00 | 10.0 | 30.0 | 60.0 |
| 1:3 | 0.104 | 0.132 | 0.181 | 0.282 | 0.403 | 0.920 | 0.761 |
| 1:2 | 0.093 | 0.130 | 0.198 | 0.331 | 0.466 | 0.784 | 0.636 |
| 1:1 | 0.079 | 0.135 | 0.224 | 0.354 | 0.431 | 0.578 | 0.463 |
| 2:1 | 0.064 | 0.064 | 0.211 | 0.315 | 0.349 | 0.358 | 0.276 |
| 3:1 | 0.062 | 0.129 | 0.201 | 0.251 | 0.279 | 0.274 | 0.216 |

| Overview S/N | BSA [mg/mL] | | | | | | |
|---|---|---|---|---|---|---|---|
| ratio BSA/Biuret | 0.00 | 1.00 | 3.00 | 6.00 | 10.0 | 30.0 | 60.0 |
| 1:3 | NA | 1.27 | 1.74 | 2.72 | 3.88 | 8.87 | 7.33 |
| 1:2 | NA | 1.41 | 2.14 | 3.57 | 5.03 | 8.47 | 6.87 |
| 1:1 | NA | 1.72 | 2.85 | 4.51 | 5.48 | 7.36 | 5.90 |
| 2:1 | NA | 0.99 | 3.29 | 4.91 | 5.45 | 5.59 | 4.31 |
| 3:1 | NA | 2.10 | 3.26 | 4.07 | 4.54 | 4.45 | 3.50 |

FIG. 39

| | 1:3 BSA/Biuret (50μL/150μL) | | | | | | |
|---|---|---|---|---|---|---|---|
| [mg/mL] | 0.00 | 1.00 | 3.00 | 5.00 | 10.0 | 30.0 | 60.0 |
| OD 1 | 0.105 | 0.130 | 0.181 | 0.281 | 0.410 | 0.936 | 0.753 |
| OD 2 | 0.105 | 0.133 | 0.181 | 0.283 | 0.395 | 0.904 | 0.769 |
| OD 3 | 0.102 | NA | NA | NA | NA | NA | NA |
| OD 4 | 0.103 | NA | NA | NA | NA | NA | NA |
| Mean | 0.104 | 0.132 | 0.181 | 0.282 | 0.403 | 0.920 | 0.761 |
| SD | 0.00 | 0.00 | 0.00 | 0.00 | 0.01 | 0.02 | 0.01 |
| CV% | 1.45% | 1.61% | 0.00% | 0.50% | 2.64% | 2.46% | 1.49% |
| S/N | NA | 1.27 | 1.74 | 2.72 | 3.88 | 8.87 | 7.33 |

| | 1:2 BSA/Biuret (65μL/130μL) | | | | | | |
|---|---|---|---|---|---|---|---|
| [mg/mL] | 0.00 | 1.00 | 3.00 | 5.00 | 10.0 | 30.0 | 60.0 |
| OD 1 | 0.093 | 0.130 | 0.197 | 0.335 | 0.467 | 0.789 | 0.653 |
| OD 2 | 0.094 | 0.130 | 0.199 | 0.326 | 0.464 | 0.778 | 0.618 |
| OD 3 | 0.091 | NA | NA | NA | NA | NA | NA |
| OD 4 | 0.092 | NA | NA | NA | NA | NA | NA |
| Mean | 0.093 | 0.130 | 0.198 | 0.331 | 0.466 | 0.784 | 0.636 |
| SD | 0.00 | 0.00 | 0.00 | 0.01 | 0.00 | 0.01 | 0.02 |
| CV% | 1.40% | 0.00% | 0.71% | 1.93% | 0.46% | 0.99% | 3.89% |
| S/N | NA | 1.41 | 2.14 | 3.57 | 5.03 | 8.47 | 6.87 |

| | 1:1 BSA/Biuret (100μL/100μL) | | | | | | |
|---|---|---|---|---|---|---|---|
| [mg/mL] | 0.00 | 1.00 | 3.00 | 6.00 | 10.0 | 30.0 | 60.0 |
| OD 1 | 0.081 | 0.136 | 0.228 | 0.358 | 0.457 | 0.578 | 0.463 |
| OD 2 | 0.081 | 0.134 | 0.220 | 0.350 | 0.404 | 0.577 | 0.463 |
| OD 3 | 0.073 | NA | NA | NA | NA | NA | NA |
| OD 4 | 0.079 | NA | NA | NA | NA | NA | NA |
| Mean | 0.079 | 0.135 | 0.224 | 0.354 | 0.431 | 0.578 | 0.463 |
| SD | 0.00 | 0.00 | 0.01 | 0.01 | 0.04 | 0.00 | 0.00 |
| CV% | 4.82% | 1.05% | 2.53% | 1.60% | 8.71% | 0.12% | 0.00% |
| S/N | NA | 1.72 | 2.85 | 4.51 | 5.48 | 7.36 | 5.90 |

FIG. 41

| | 2:1 BSA/Biuret (130μL/65μL) | | | | | | |
|---|---|---|---|---|---|---|---|
| [mg/mL] | 0.00 | 1.00 | 3.00 | 6.00 | 10.0 | 30.0 | 60.0 |
| OD 1 | 0.058 | 0.062 | 0.214 | 0.298 | 0.352 | 0.365 | 0.278 |
| OD 2 | 0.071 | 0.065 | 0.207 | 0.331 | 0.346 | 0.350 | 0.274 |
| OD 3 | 0.062 | NA | NA | NA | NA | NA | NA |
| OD 4 | 0.065 | NA | NA | NA | NA | NA | NA |
| Mean | 0.064 | 0.064 | 0.211 | 0.315 | 0.349 | 0.358 | 0.276 |
| SD | 0.01 | 0.00 | 0.00 | 0.02 | 0.00 | 0.01 | 0.00 |
| CV% | 8.56% | 3.34% | 2.35% | 7.42% | 1.22% | 2.97% | 1.02% |
| S/N | NA | 0.99 | 3.29 | 4.91 | 5.45 | 5.59 | 4.31 |

| | 3:1 BSA/Biuret (150μL/50μL) | | | | | | |
|---|---|---|---|---|---|---|---|
| [mg/mL] | 0.00 | 1.00 | 3.00 | 6.00 | 10.0 | 30.0 | 60.0 |
| OD 1 | 0.063 | 0.124 | 0.192 | 0.223 | 0.244 | 0.294 | 0.233 |
| OD 2 | 0.062 | 0.134 | 0.209 | 0.278 | 0.314 | 0.253 | 0.198 |
| OD 3 | 0.063 | NA | NA | NA | NA | NA | NA |
| OD 4 | 0.058 | NA | NA | NA | NA | NA | NA |
| Mean | 0.062 | 0.129 | 0.201 | 0.251 | 0.279 | 0.274 | 0.216 |
| SD | 0.00 | 0.01 | 0.01 | 0.04 | 0.05 | 0.03 | 0.02 |
| CV% | 3.87% | 5.48% | 6.00% | 15.5% | 17.7% | 10.6% | 11.5% |
| S/N | NA | 2.10 | 3.26 | 4.07 | 4.54 | 4.45 | 3.50 |

KIT AND METHOD OF REDUCING HUMAN ERROR DURING IMPLANTED INFUSION PUMP REFILLING

BACKGROUND OF THE INVENTION

1. Field of the Invention

This invention relates to a kit or system for more safely filling an implanted infusion pump, for example, by determining or detecting whether "pocket fill" has occurred. The invention also includes a method of determining or detecting whether pocket-fill has occurred and/or of more safely filling an implanted infusion pump. The implanted infusion pump may be of the type that dispenses baclofen.

2. Discussion of Background Information

Implantable infusion pumps are generally safe and effective forms of treatment for approved uses. An example of the same is described in U.S. Pat. No. 7,044,932 to BORCHARD et al., the entire disclosure of which is herein expressly incorporated by reference. However, one of the safety concerns of implantable infusion pumps is human error during the pump refill process.

One type of error that can occur in a refill process is that the health care professional fails to inject the medicine into the designated reservoir of the infusion pump, and instead, injects the medicine into the human tissues surrounding the infusion pump. This can result in a number of safety concerns for the patient depending on the type of medicine used for injection.

Errors in the context of the invention include those associated with underdose, overdose, and adverse events. In addition, such errors can likely lead to either an overdose (injection of too much medicine directly into the body) or under-dose, leading potentially to withdrawal reactions (from the lack of medication reaching the pump and resultant delivery target, resulting in a complete withdrawal of medication from the patient when the reservoir becomes empty). These errors are referred to as "pocket fills" referring to the injection of some or all of the prescribed drug into the patient's subcutaneous tissue, which includes the pump pocket or area under the skin where the pump is placed, which may include a pocket of fluid that often surrounds foreign objects implanted into the body. This can lead to a series of serious medical events, which could include death. One should also appreciate that, for some pumps, one cannot readily determine (or directly measure) the volume of fluid that actually makes it into the pump reservoir.

Implantable infusion pumps have been designed to ensure the highest level of safety when delivering medicine within the human body. In order to maintain that safety, the pumps have been engineered to ensure that exposure to foreign materials (anything other than medicine which was specifically developed for this use) is minimized to prevent pump malfunction or infection. These efforts have led to pump systems that are highly effective in preventing unintended exposure to protein inside the pump reservoir.

Foreign objects, such as implantable infusion pumps, can be disruptive to the human body. In an effort to protect the body from the foreign object, the immune system may respond by surrounding the foreign object with fat, collagen, and/or vasculature in an effort to create a barrier between the foreign object and the body. In doing so, the body may create fluid pockets that directly surround the pump and these fluids are filled with a variety of things, including proteins.

Post implantation, the infusion pump requires periodic refilling of the drug product intended for targeted delivery via the infusion pump.

The infusion pump refill procedure is typically broken into five sub-procedures as follows:

1. Patient prep—this involves getting the patient into a good position to conduct the procedure. Cleaning the site overlaying the infusion pump in preparation for a subcutaneous injection, and preparing the sterile field with the instruments (syringes, needles, medicine, etc.) that will be used in the procedure (generally described in the infusion pump refill kit instructions—which can be provided or otherwise available such as from a website).
2. Placing a needle into the pump reservoir—this is the procedure in which the health care professional attempts to secure a direct line with a needle into the designated septum of the infusion pump reservoir, which occurs via subcutaneous injection. This process is often challenging and the health care professional may supplement their own training and skill with other detection techniques, including but not limited to the use of ultrasound.
3. Withdrawing the remaining drug in the reservoir—before refilling the pump, the pump must be completely empty as the refills are typically designated to fill the full volume of the pump reservoir. This is also an opportunity for physicians to identify how much medication was left in the pump and compare it to what was expected to be leftover (based on information available in the pump and in some devices, extractable through a handheld, wireless programming device). This is the primary method of physicians identifying if they have hit a "pocket" or if they have been able to access the pump reservoir. If a physician were to hit a "pocket" they may extract a clear fluid as well, potentially due to the lack of vasculature directly surrounding the pump.
4. Refilling the pump—this is when the health care professional injects the new medication into the pump via subcutaneous injection through the designated pump septum. This is also the place where a health care professional might inject the medication instead into a "pocket", delivering the medication inadvertently directly into the patient subcutaneously.
5. Removal, cleanup, reprogramming—after the pump is filled, the pump is reprogrammed for administration of the newly placed drug, typically using the same handheld device and the patient is cleaned for discharge.

At each time in which the pump is filled or refilled, there is a risk that the pump will not be filled correctly, as explained above. There remains a need in the field to improve the safety at the filling and refilling stage.

SUMMARY OF THE INVENTION

The invention aims to improve the safety of treating with implantable infusion pump technology by providing an embodiment that would allow health care practitioners or trained assistants, when performing the withdrawing stage (as related to pump filling or refilling), to access the fluid that they are extracting from the body and to prevent the filling or refilling stage until there is assurance that the pump reservoir has been correctly located.

Embodiments of the invention include methods of testing the fluid that has been removed from the body with a color-changing composition that, upon contact with the withdrawn fluid, can detect the existence of proteins. If no color change occurs, the health care professional will have an indication that they have correctly accessed the pump reservoir. This method can be employed as part of the pump refill kit and can be performed by physicians, hospital personnel, ancillary healthcare practitioners or trained staff.

Non-limiting embodiments of the invention include:

A fluid-withdrawing device such as a syringe for withdrawing fluid.

A bag or container containing a color-changing composition such as biuret and having a connecting interface allowing the syringe to connect thereto and to receive therein the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

Non-limiting embodiments of the invention include:

A fluid-withdrawing device such as a syringe for withdrawing fluid.

A bag or container containing a color-changing composition such as biuret and having a connecting interface allowing the syringe to connect thereto and to receive therein the withdrawn fluid. A label or tag is arranged on or associated with the bag or container to provide a visual indicator to the user. If the introduced withdrawn fluid contains protein, it will cause the color changing composition to change color upon contact therewith. This color may be configured to match a color on the adjoining label or tag that visually indicates to a user that the fluid has tested positive for containing protein. If the introduced fluid does not contain protein (or contains protein in an amount below the detection threshold), no color change will be detected. The tag may contain another color indicator associated with a negative test result, i.e., if the color of the fluid matches the color on the tag, the tested withdrawn fluid does not contain protein (or contains protein in an amount below the detection threshold), Non-limiting embodiments of the invention include:

A fluid-withdrawing device such as a syringe for withdrawing fluid.

A needle, medical tubing for accessing the pump reservoir, and a valve device for selectively stopping flow through the tubing.

A bag or container containing a color-changing composition such as biuret and having a connecting interface allowing the syringe to connect thereto and to receive therein the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

A package or container for containing and storing the above-noted items.

Non-limiting embodiments of the invention include:

A fluid-withdrawing device such as a syringe for withdrawing fluid.

A needle, medical tubing for accessing the pump reservoir, and a valve device for selectively stopping flow through the tubing.

A bag or container containing a color-changing composition such as biuret and having a connecting interface allowing the syringe to connect thereto and to receive therein the withdrawn fluid. A label or tag is arranged on or associated with the bag to provide a visual indicator to the user. If the introduced withdrawn fluid contains protein, it will cause the color changing composition to change color upon contact therewith. This color will generally match a color on the tag that visually indicates to a user that the fluid has tested positive for containing protein. If the introduced fluid does not contain protein (or contains protein in an amount below the detection threshold), no color change will be detected. The tag may contain another color indicator associated with a negative test result, i.e., if the color of the fluid matches the color on the tag, the tested withdrawn fluid does not contain protein (or contains protein in an amount below the detection threshold).

A package or container for containing and storing the above-noted items which can include instructions or information for obtaining instructions elsewhere such as from a website.

Non-limiting embodiments of the invention include:

A fluid-withdrawing device such as a syringe for withdrawing fluid.

A needle, medical tubing for accessing the pump reservoir, and a valve device for selectively stopping flow through the tubing.

A bag or container containing a color-changing composition such as biuret and having a connecting interface with integral one-way valve (or device containing the same) allowing the syringe to connect thereto and to receive therein the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

A package or container for containing and storing the above-noted items.

Non-limiting embodiments of the invention include:

A fluid-withdrawing device such as a syringe for withdrawing fluid.

A needle, medical tubing for accessing the pump reservoir, and a valve device for selectively stopping flow through the tubing.

A bag or container containing a color-changing composition such as biuret and having a connecting interface with integral one-way valve allowing the syringe to connect thereto and to receive therein the withdrawn fluid. A label or tag is arranged on or associated with the bag to provide a visual indicator to the user. If the introduced withdrawn fluid contains protein, it will cause the color changing composition to change color upon contact therewith. This color will generally match a color on the label, tag or instructions that visually indicates to a user that the fluid has tested positive for containing protein. If the introduced fluid does not contain protein (or contains protein in an amount below the detection threshold), no color change will be detected. The tag may contain another color indicator associated with a negative test result, i.e., if the color of the fluid matches the color on the tag, the tested withdrawn fluid does not contain protein (or contains protein in an amount below the detection threshold).

A package or container for containing and storing the above-noted items.

Non-limiting embodiments of the invention include, among other things:

A fluid-withdrawing device such as a non-needle or non-luer-lock type syringe for withdrawing fluid;

A one-way valve for connecting the injection device to a container or bag; and

A bag or container containing a color changing composition such as biuret in either liquid form or as a coating disposed inside the container or bag. If the introduced withdrawn fluid contains protein, it will cause the color changing composition to change color upon contact therewith. If the introduced fluid does not contain protein (or contains protein in an amount below the detection threshold), no color change will be detected.

Non-limiting embodiments of the invention include:

A fluid-withdrawing device such as a needle or needle-luer-lock type syringe for withdrawing fluid; and A vial, bottle, bag or container containing a color changing composition such as biuret in either liquid form or as a coating disposed inside the container or bag. A portion of the container, such as the container wall or a pierceable cap, allows for the needle to pass there-through to introduce the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

Non-limiting embodiments of the invention include:

A fluid-withdrawing device having a needle for withdrawing fluid; and

A vial containing a color changing composition such as biuret in either liquid form or as a coating disposed inside the vial. A portion of the vial such as a pierceable cap allows for the needle to pass there-through to introduce between 2 to 6 milliliters the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

Non-limiting embodiments of the invention include:

A fluid-withdrawing device having a needle for withdrawing fluid. The fluid-withdrawing device contains therein a color changing composition such as biuret in either powder form, liquid form or as a coating disposed inside and can receive therein between 1 and 10 milliliters the withdrawn fluid. If the introduced withdrawn fluid contains protein, it will cause the color changing composition to change color upon contact therewith. If the introduced fluid does not contain protein (or contains protein in an amount below the detection threshold), no color change will be detected.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein: The figures are intended to show basic features, functioning and aid in understanding and may or may not show features or details which are utilized in commercial embodiments.

FIG. 1 shows an exemplary container or bag containing a protein-detecting composition and a connecting interface having an integral one-way valve in accordance with the invention;

FIG. 2 shows a top view of FIG. 1;

FIG. 3 shows a bottom view of FIG. 1;

FIG. 4 shows how an injection device can be aligned with the connecting interface of the container or bag containing the protein-detecting composition;

FIG. 5 shows the injection device connected to the connecting interface of the container or bag and injecting the withdrawn fluid into the container or bag so that it can contact the protein-detecting composition;

FIG. 6 shows a partial cross-section of an exemplary connecting interface system that can be used with the invention. The connecting interface is sealingly connected to a wall of the container or bag and includes a male luer-lock that can be connected with a standard luer-lock connector of an injection device such as a syringe;

FIG. 7 shows an enlarged view of the connecting interface having an integral one-way valve in accordance with the invention;

FIG. 8 shows a top view of FIG. 7;

FIG. 9 shows a bottom view of FIG. 7;

FIG. 10 shows an exemplary container or bag containing a protein-detecting composition and a connecting interface having an integral one-way valve in accordance with another embodiment of the invention. This embodiment includes a label having two distinct color regions at least one of which is indicative of the protein-detecting composition color change;

FIG. 11 shows a bottom view of FIG. 10;

FIG. 12 shows an exemplary container or bag containing a protein-detecting composition and a connecting interface having an integral one-way valve in accordance with another embodiment of the invention. This embodiment includes a label having multiple, e.g., three, distinct color regions at least one of which is indicative of the protein-detecting composition color change;

FIG. 13 shows a bottom view of FIG. 12;

FIG. 14 shows an exemplary container or bag containing a protein-detecting composition and a connecting interface having an integral one-way valve in accordance with another embodiment of the invention. This embodiment includes a tag having at least one color region which is indicative of the protein-detecting composition color change;

FIG. 15 shows a bottom view of FIG. 14;

FIG. 16 shows an exemplary container or bag containing a protein-detecting composition and a connecting interface having an integral one-way valve in accordance with another embodiment of the invention. This embodiment includes a tag having plural color regions, e.g., two, at least one of which is indicative of the protein-detecting composition color change;

FIG. 17 shows a bottom view of FIG. 16;

FIG. 18 shows how a non-needle or non-luer-lock type injection device can be aligned with the connecting interface of a one-way valve and how the one-way valve can be aligned with an inlet tube of a container or bag containing the protein-detecting composition;

FIG. 19 shows the injection device connected to the one-way valve which in turn is connected to the container or bag and injecting the withdrawn fluid into the container or bag so that it can contact the protein-detecting composition, which in this embodiment has the form of a liquid composition disposed inside the bag;

FIG. 20 shows how a non-needle injection device can be aligned with the connecting interface of a one-way valve and how the one-way valve can be aligned with an inlet tube of a container or bag containing the protein-detecting composition;

FIG. 23 shows an injection device using a needle that can be injected into a pierceable portion of a bag or container to introduce the withdrawn fluid without the need for a one-way valve. The container contains therein a protein detecting composition that can change color when contacted by protein;

FIG. 24 shows an injection device using a needle that can be injected into a pierceable cap of a bottle or vial to introduce the withdrawn fluid without the need for a one-way valve. The bottle or vial contains a protein detecting composition that can change color when contacted by protein;

FIG. 29 is a table illustrating Gornall biuret solution;

FIG. 30 is a table illustrating Weichselbaum biuret solution;

FIG. 31 is a table illustrating a Modified biuret solution;

FIG. 32 is a table illustrating test results;

FIGS. 34 and 35 are tables illustrating Weichselbaum solution performance;

Figure 36:
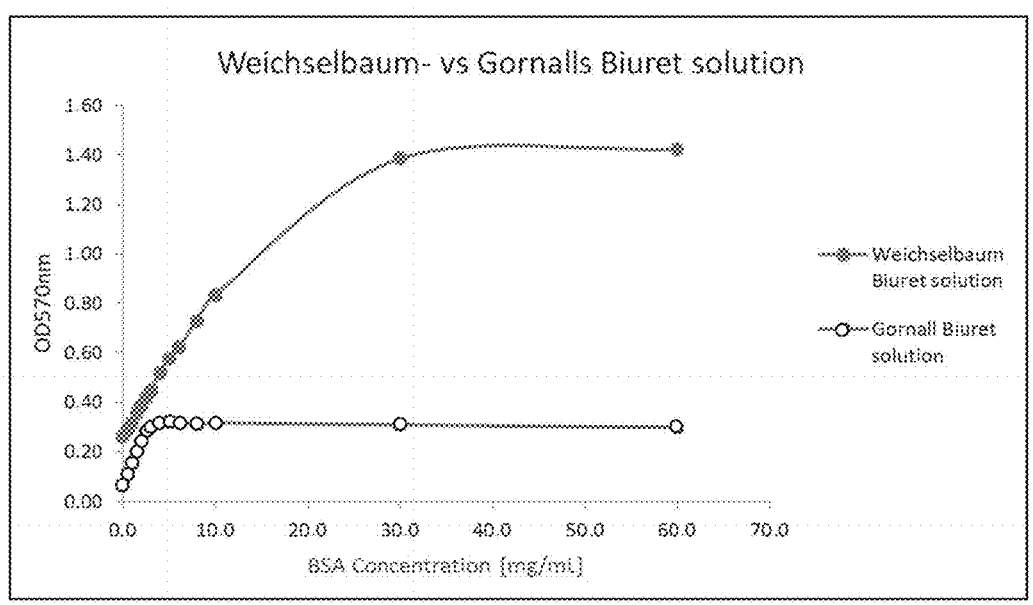
Figure 38:
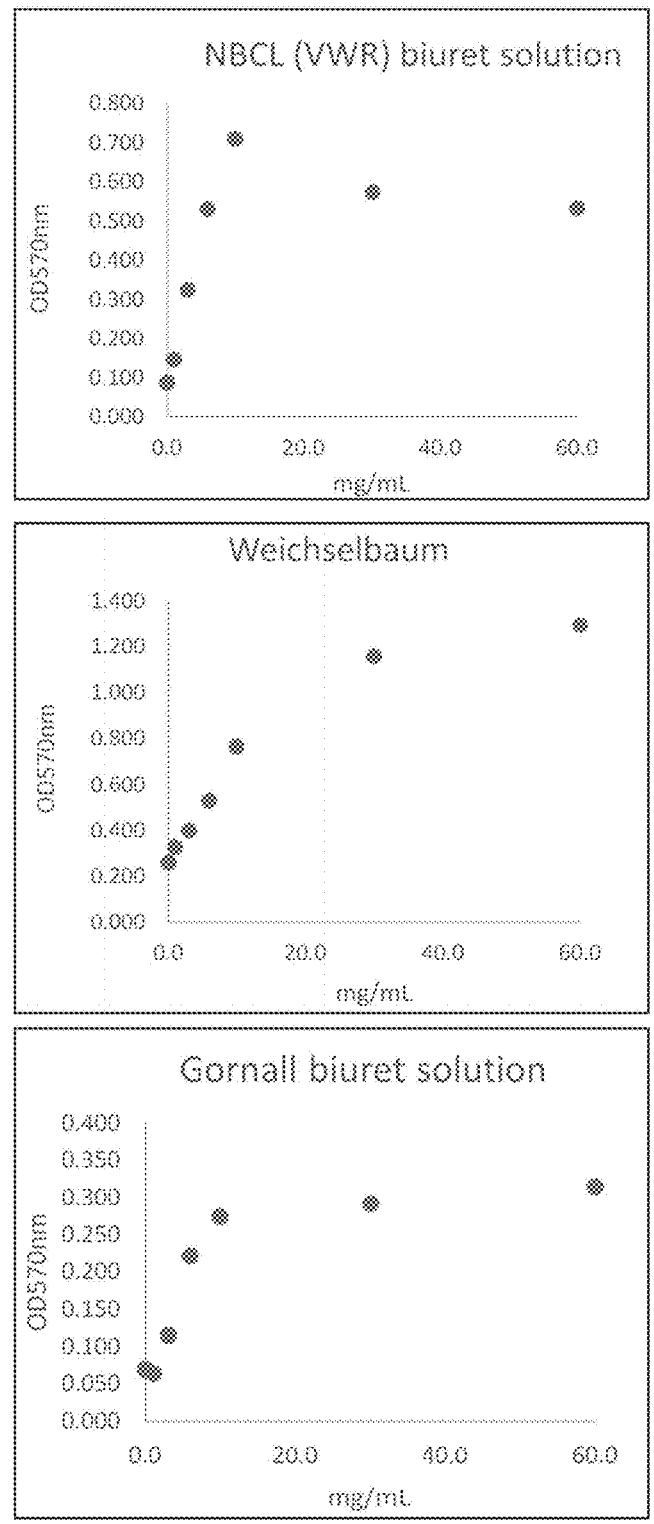
Figure 40:
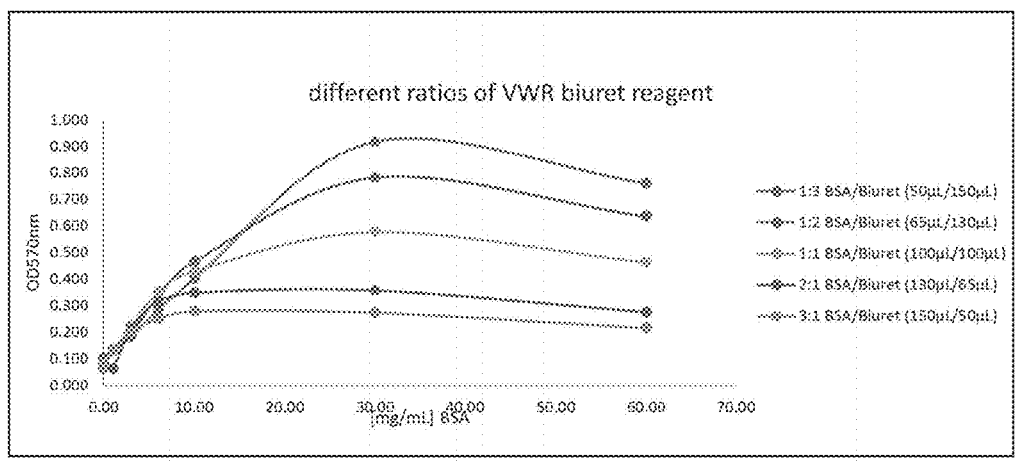
Figures 44, 45:
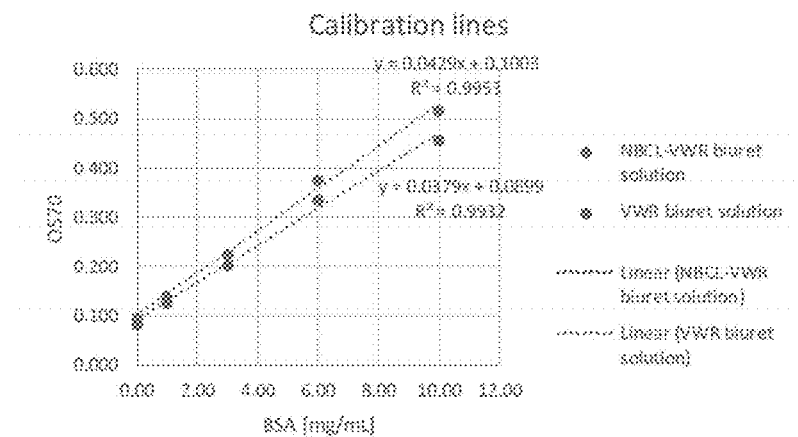

FIG. 36 a graph comparing biuret solutions;

FIG. 37 shows tables illustrating Modified biuret solution;

FIG. 38 shows graphs comparing biuret solutions;

FIG. 39 is a table illustrating biuret reagent solution performance;

FIG. 40 a graph comparing different ratios of modified biuret solution reagents;

FIG. 41 are tables illustrating BSA/biuret solutions;

FIG. 42 are tables illustrating BSA/biuret solutions;

Figure 43:
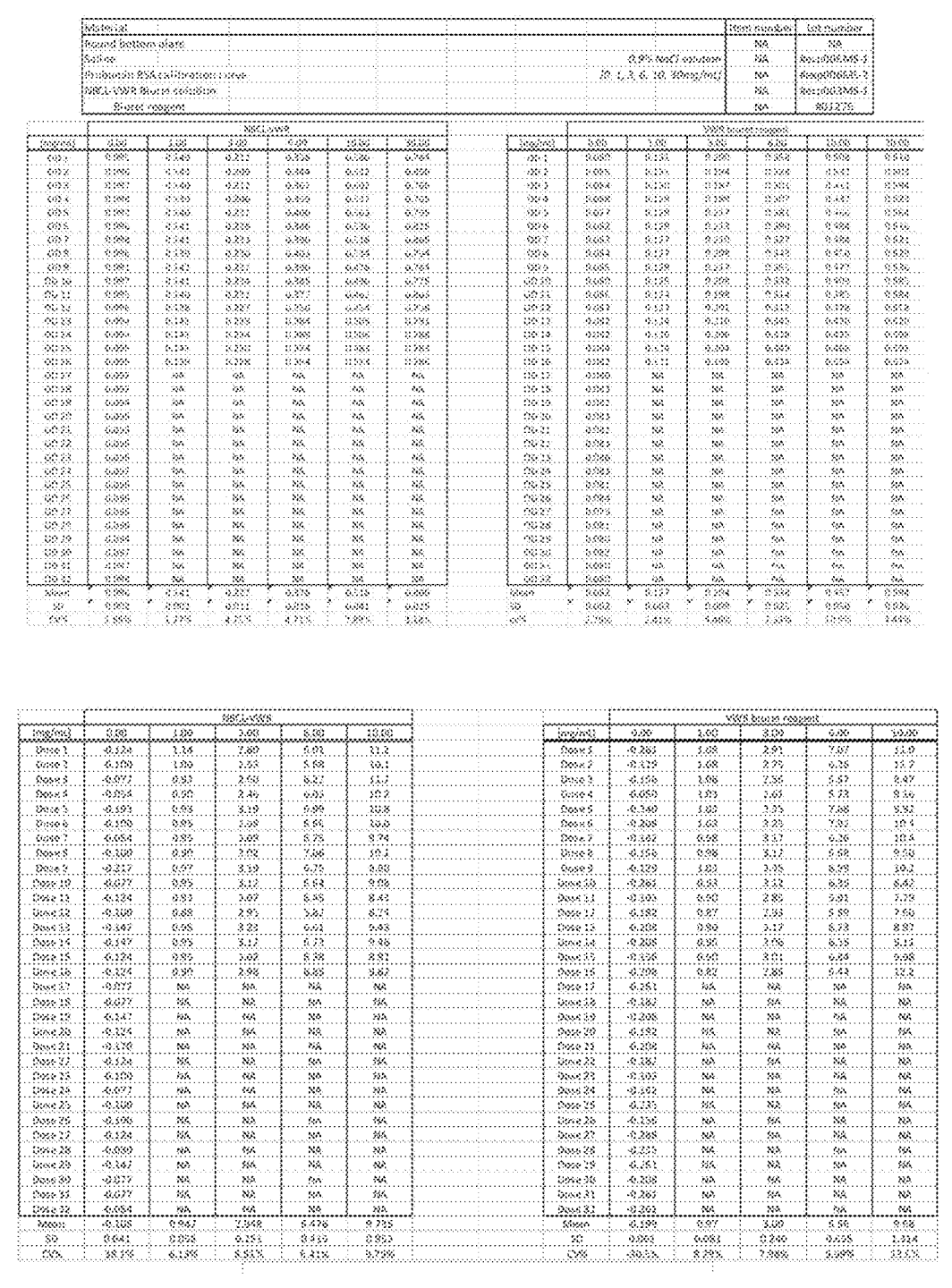

FIG. 43 are tables illustrating NBCL-VWR biuret solutions;

FIG. 44 is a graph illustrating calibration lines;

FIG. 45 is a table illustrating concentrations; and

Figure 46:
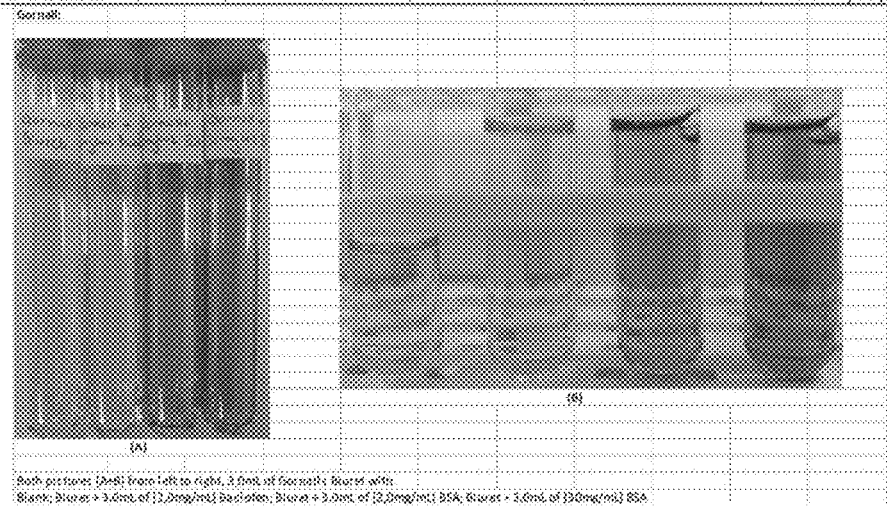

FIG. 46 is a table illustrating Weichselbaum solution performance.

DETAILED DESCRIPTION OF THE INVENTION

The present invention is further described in the detailed description which follows, in reference to exemplary embodiments.

Figure 27:
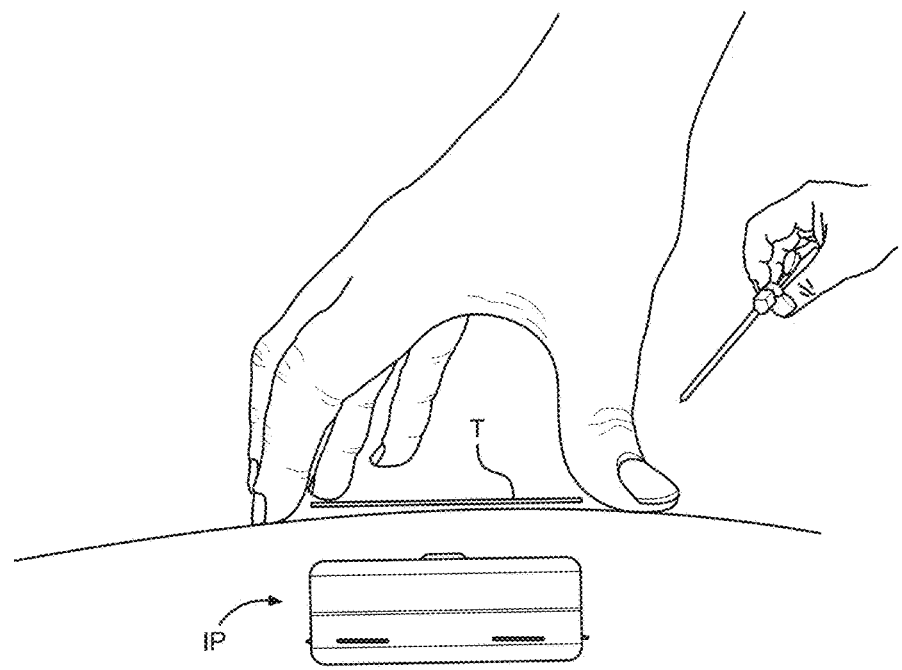
FIG. 27 shows an exemplary way in which one can access an implanted infusion pump and attempt to locate the pump reservoir for filling the same.
Figure 28:
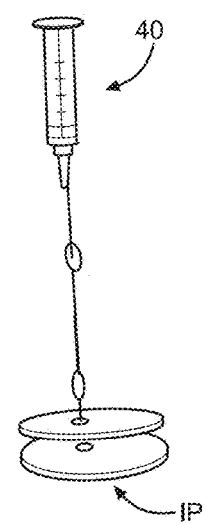
FIG. 28 shows a typical arrangement used for accessing and filling an implanted infusion pump.

FIGS. 27 and 28 show an exemplary implanted infusion pump IP disposed beneath skin while a user or medical professional utilizes an access template T and shows some of the devices used to perform this function. These devices include a syringe, a needle as well as other components associated with these devices such as connectors, connecting ports, pinch clamp valves, needles and medical tubing. The invention, in embodiments, utilizes a number of these devices (see e.g., FIG. 28) such as a syringe having a luer-lock interface, a section of medical tubing having one end with a luer-lock connector for connecting to the syringe and an opposite end connected to a needle which will access the reservoir of the pump. A hose-pinch type valve can be arranged on the tubing to selectively stop the flow through the tubing.

Figure 1:
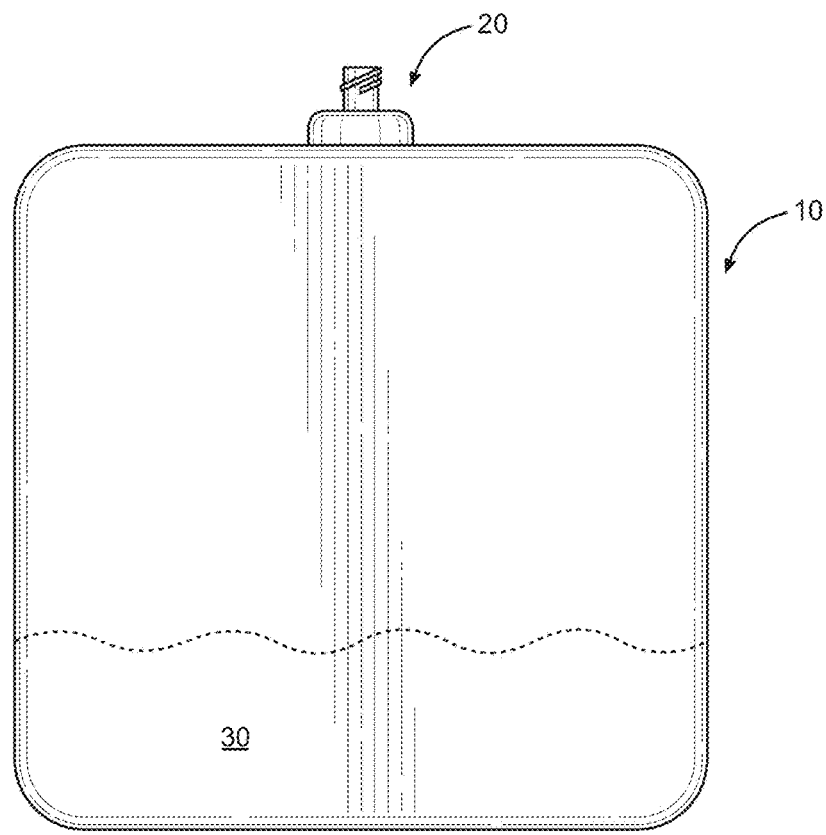
Figure 2:
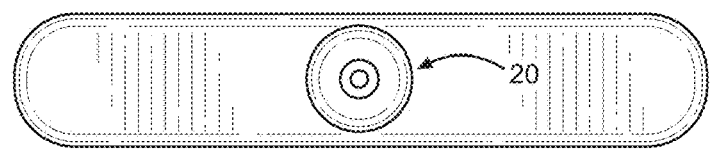
Figure 3:
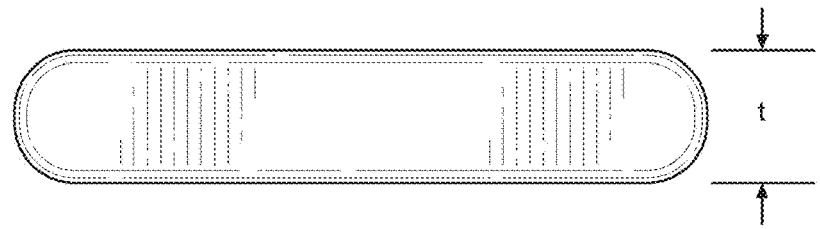

As shown in FIGS. 1-3, the invention also utilizes an exemplary container or bag 10 which is sized and configured to contain a predetermined amount of protein-detecting composition 30. In accordance with non-limiting aspects of the invention, this composition 30 is a biuret solution which changes color when contacted by a fluid containing protein. The container or bag 10 can have a variety of forms which include vials, bottles and bags that resemble IV solution bags which can assume a generally flat configuration when empty. At least a portion (e.g., a window area) or all, or nearly all, of the container 10 can be transparent or translucent in order that a color change can be detected from outside the container. When having the form of a bag, the container 10 can have a thickness "t" (see FIG. 3) of only one to a few millimeters when in the empty state. Non-limiting exemplary volumes for the bag 10 include from about 15 ml (milliliters) to 100 ml or more. Non-limiting exemplary volumes for the composition 30 include from about a few ml to 30 ml or more with 5 ml being appropriate. The volume of the container 10 can also be determined in the range of, e.g., about 3 to 4 times, that of the volume of composition 30 contained therein.

As is shown in FIGS. 1-6, the container or bag 10 includes a connecting interface 20 that allows one to connect an injection device or syringe 40 thereto. In the exemplary embodiment, the interface 20 includes a luer-lock connector 21 which can be connected to a luer-lock connector 41 of the syringe 40. As is shown in FIGS. 6-9, the interface 20 also includes an insertion end 22, a container attaching groove 23 and an integral one-way valve. The groove 23 is configured to sealing connect the interface to a wall 11 of the container 10 and can be sealingly connected using a number of techniques such as, e.g., adhesive bonding or ultrasonic welding. The one-way valve 24 can have the form of a slit which elastically spreads apart when fluid is forced through the interface 20 but which then elastically returns to a closed position when fluid is no longer forced through the interface 20. The invention also contemplates utilizing an interface 20 of the type disclosed in U.S. Pat. No. 9,227,048, the disclosure of which is herein expressly incorporated by reference, as well as one that does not include an integral one-way valve which is instead separately employed. In the case where the interface 20 is of the type disclosed in U.S. Pat. No. 9,227,048, the withdrawn fluid can be injected via a needle of the syringe 40 into the interface without the syringe 40 being connected to the interface 20.

Figure 5:
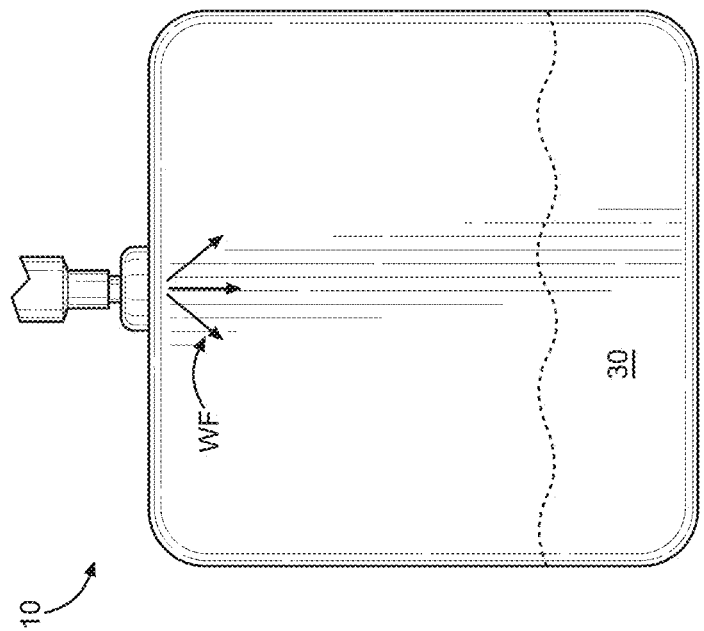
Figure 4:
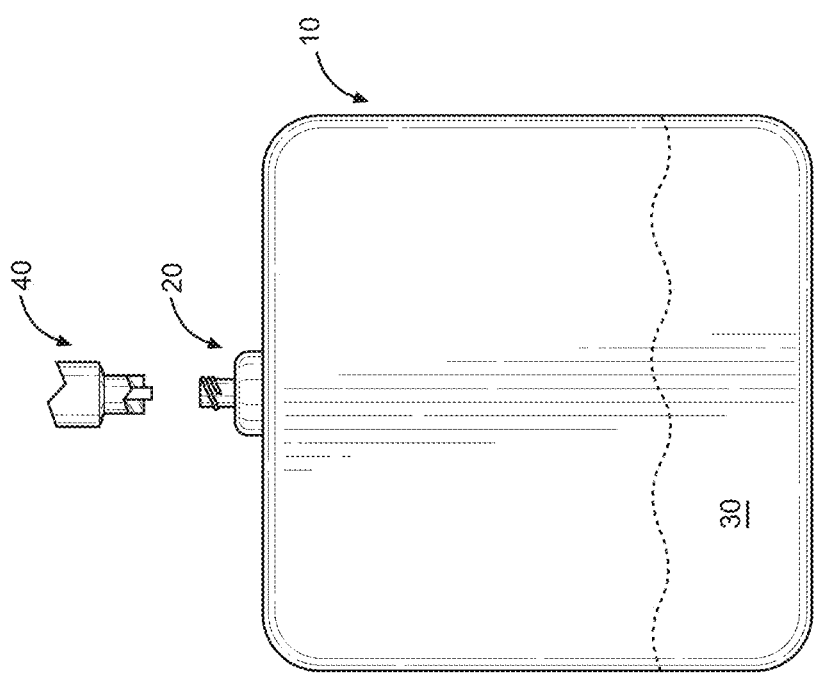
Figure 7:
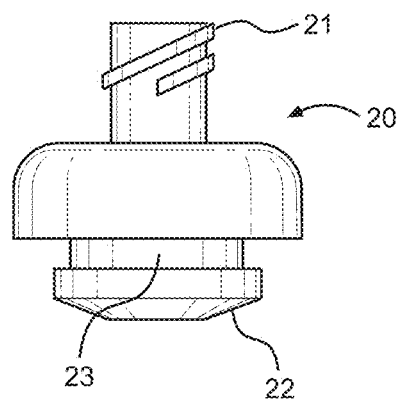
Figure 8:
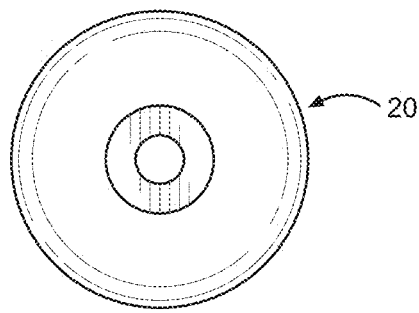
Figure 9:
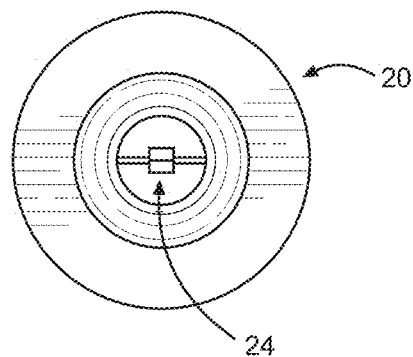
Figure 19:
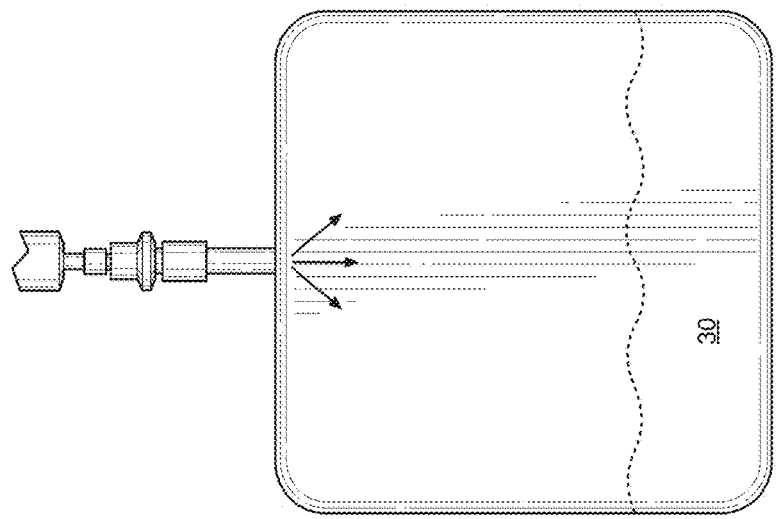
Figure 20:
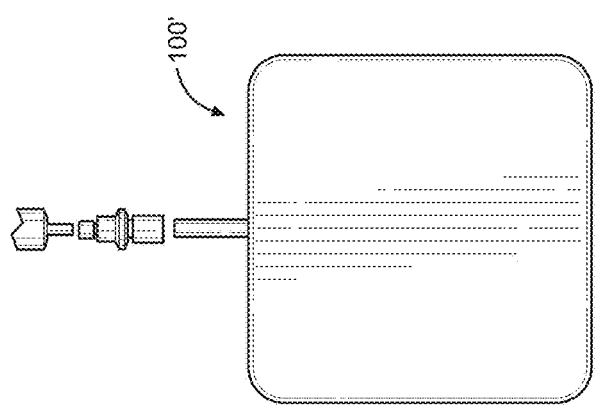

A user will typically connect the syringe 40 to the interface 20 as shown in FIGS. 4 and 5 after fluid is withdrawn in an attempt to re-fill an implanted pump in a manner similar to that shown in FIGS. 19 and 20. Since the user will want to ensure that the withdrawn fluid is from the pump reservoir and not a pocket fill injection, the user can inject the withdrawn fluid WF into the container 10 as shown in FIG. 5. When this happens, the injected withdrawn fluid WF will come into contact with the protein-detecting composition 30. After contact, the composition 30 can react (or not react) in a number of ways which include:

A. No color change (or a change below a threshold value);

B. A color change indicative of protein detection. Examples include a change from clear or translucent to violet, or a change from blue or light blue to violet (but the actual color is not critical, and can be any color whose appearance may be observed, either through the naked eye or with machine assistance);

C. A color change indicative of a medicine contained in the infusion pump; and

D. A color change indicative of a medicine and a protein contained in the infusion pump.

In the case of A, where no color change occurs, this can provide a visual indication that no protein was detected in the fluid WF. The user can thus be assured that the withdrawn fluid is from the pump reservoir and not from a pocket fill injection. If the pump reservoir has not yet been emptied, this can now be completed and the infusion pump refilled. Note that while "no color change" is referred to here, this of course encompasses a situation in which a color change occurs but is minor and is considered to be below a threshold value.

In the case of B, where a color change indicates protein detection has occurred, this will provide a visual indication that protein was detected in the fluid WF. The user can thus be informed that an error was made in that the withdrawn fluid is likely from a pocket fill location rather than from the pump reservoir. The user thus knows not to attempt refilling of the infusion pump and to instead attempt again to correctly locate the pump reservoir. This can occur by the obtaining another needle, locating the pump reservoir and injecting the needle in that location. The withdrawn fluid from this new location can be tested using a new syringe 40 and a new container 10 containing the protein-detecting composition 30. In this case, the original syringe 40, container 10, tubing and needle can be safely discarded.

In the case of C, where a color change occurs detecting only a medicine, this can provide a visual indication that no protein was detected in the fluid WF. The user can thus be assured that the withdrawn fluid is from the pump reservoir and not from a pocket fill injection. If the pump reservoir has not yet been emptied, this can now be completed and the infusion pump refilled.

In the case of D, where a color change indicates protein detection and medicine detection has occurred, this will provide a visual indication that both medicine and protein was detected in the fluid WF. The user can thus be informed that something is wrong with the implanted pump. The area of tissue around the pump should not contain any significant amount of medicine and the pump reservoir should not contain any protein. The user thus knows not to attempt refilling of the infusion pump and to instead take corrective action(s).

Figure 10:
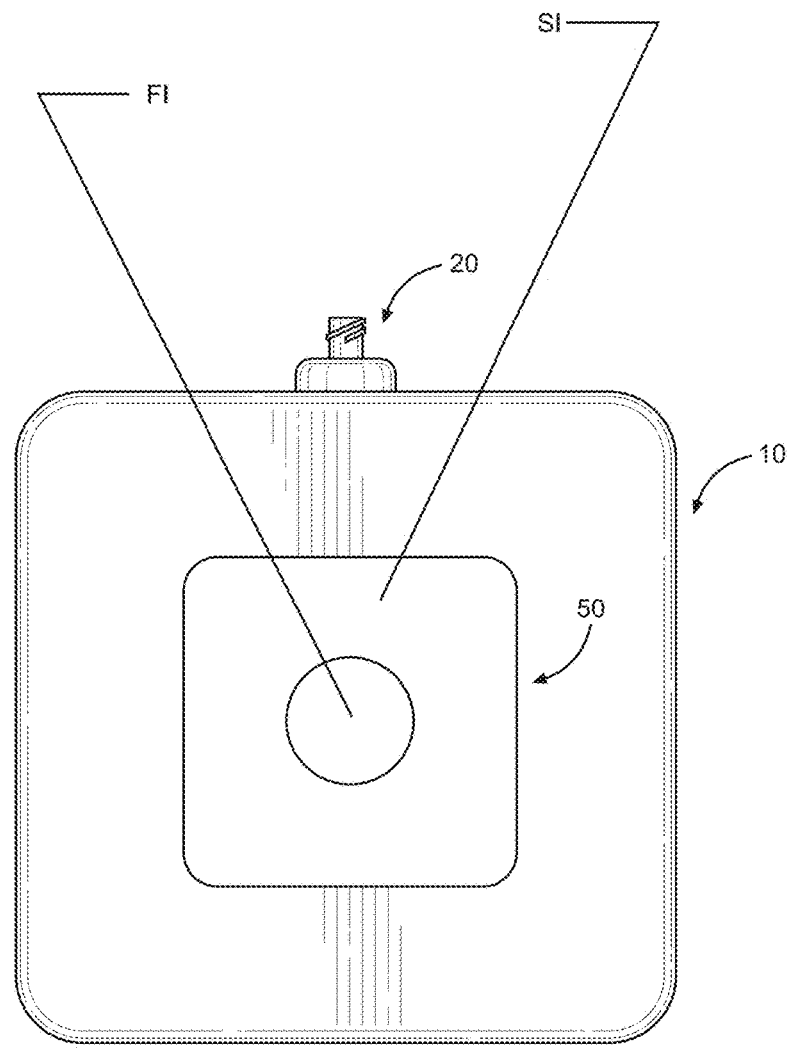
Figure 11:
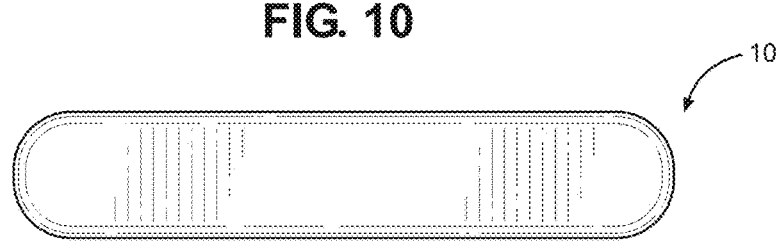

FIGS. 10 and 11 show another embodiment of a container or bag 10 which is sized and configured to contain a predetermined amount of protein-detecting composition 30. In accordance with non-limiting aspects of the invention, this composition 30 is a biuret solution which changes color when contacted by a fluid containing protein. Examples of the biuret solution can be found in Table 1 below. As with the embodiment of FIG. 1, the container or bag 10 can have a variety of forms which include vials, bottles and bags that resemble IV solution bags which can assume a generally flat configuration when empty. Non-limiting exemplary volumes for the bag 10 include from about 15 ml (milliliters) to 100 ml or more, if necessary. Non-limiting exemplary volumes for the composition 30 include from about a few ml to 30 ml or more with 5 ml being appropriate. The volume of the container 10 can also be determined in the range of, e.g., about 3 to 4 times, that of the volume of composition 30 contained therein. In this embodiment, the container 10 need not be transparent or translucent except for the first indicator FI. The second indicator area SI can be the same or substantially the same as the composition 30 after detecting protein and undergoing a color change. Thus, if the area FI assumes a color that sufficiently matches the color of the area SI, the user will be informed that the tested withdrawn fluid contains protein and appropriate action can be taken as described above. In the embodiment of FIG. 10, the areas FI and SI can have the form of a label 50. Non-limiting examples include printing the label 50 directly onto the container 10 or separately providing a label 50 that is adhesively attached to the container 10.

Alternatively, in the embodiment of FIGS. 10 and 11, the container or bag 10 is substantially transparent or translucent and the label 50 contains a first indicator area FI and a second indicator area SI. Either one of these areas can be the same or substantially the same as the composition 30 after detecting protein and undergoing a color change while the other area is that of the original non-color changed composition. Thus, if the area FI that will change color assumes a color that sufficiently matches the color of the area SI (or vice versa), the user will be informed that the tested withdrawn fluid contains protein and appropriate action can be taken as described above.

Figure 12:
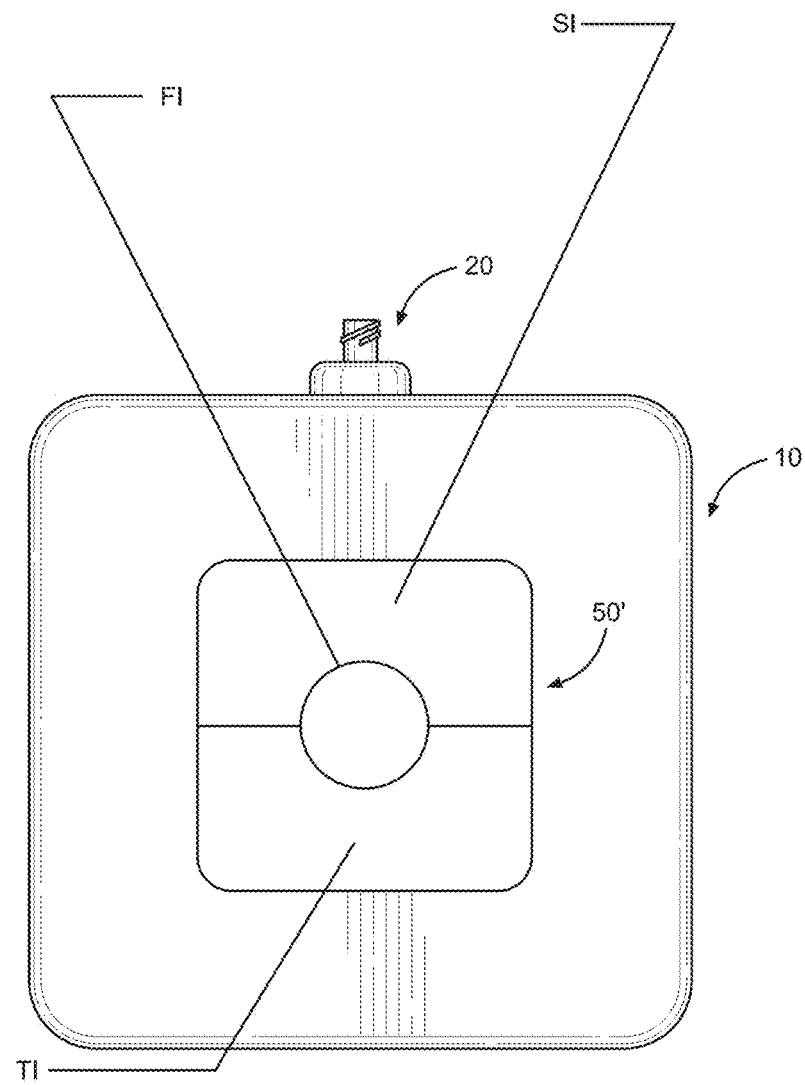
Figure 13:

FIGS. 12 and 13 show another embodiment of a container or bag 10 which is sized and configured to contain a predetermined amount of protein-detecting composition 30. In this embodiment, the container 10 need not be transparent or translucent except for the first indicator FI. The second indicator area SI can be the same or substantially the same as the composition 30 after detecting protein and undergoing a color change. The third indicator area TI can be the same or substantially the same as the composition 30 after detecting only medicine and undergoing a color change. Thus, if the area FI assumes a color that sufficiently matches the color of the area SI, the user will be informed that the tested withdrawn fluid contains protein and appropriate action can be taken as described above. On the other hand, if the area FI assumes a color that sufficiently matches the color of the area TI, the user will be informed that the tested withdrawn fluid contains only medicine and appropriate action can be taken as described above. In the embodiment of FIG. 12, the areas FI, SI and TI can have the form of a label 50'. Non-limiting examples include printing the label 50' directly onto the container 10 or separately providing a label 50' that is adhesively attached to the container 10.

Figure 14:
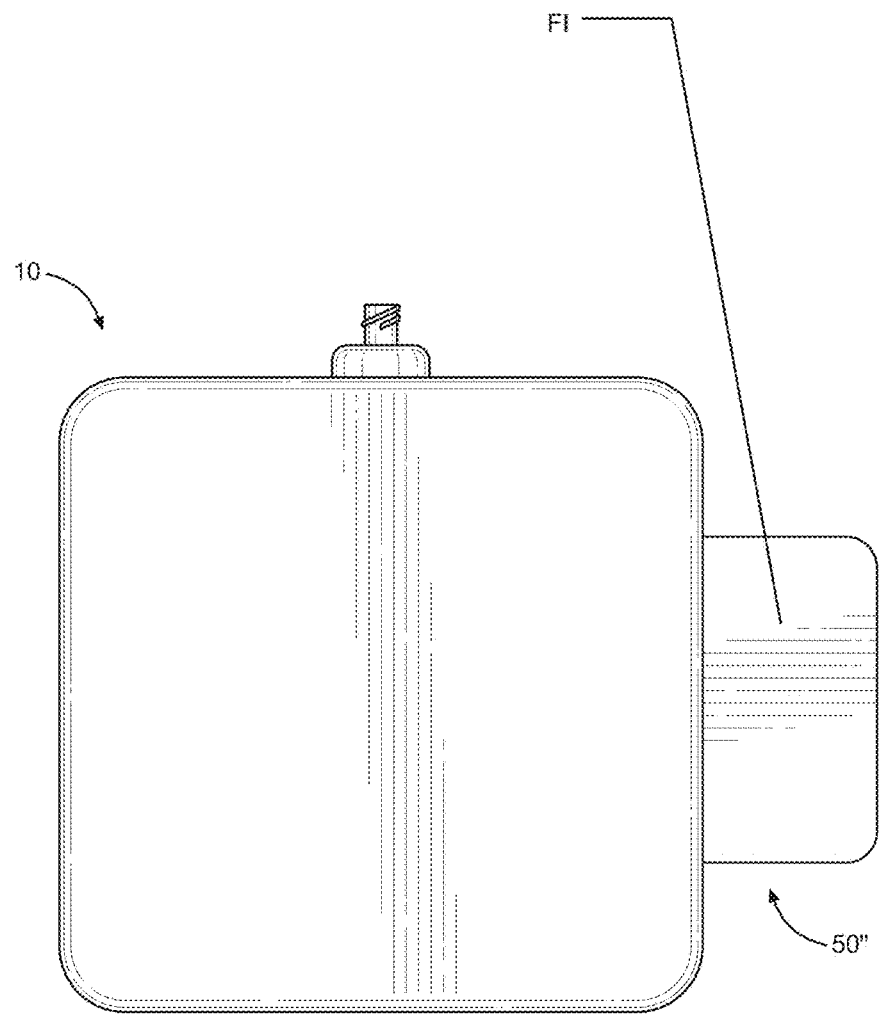
Figure 15:
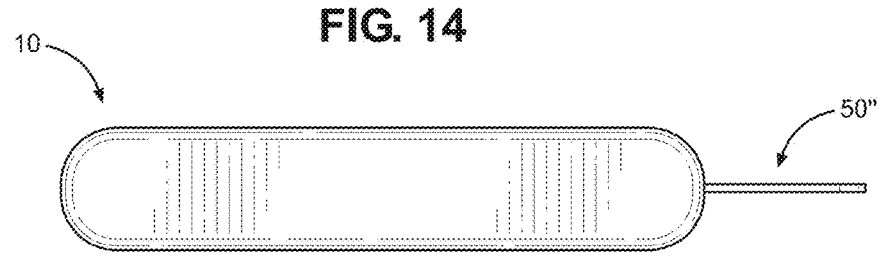

FIGS. 14 and 15 show another embodiment of a container or bag 10 which is sized and configured to contain a predetermined amount of protein-detecting composition 30. In this embodiment, the container 10 is preferably transparent or translucent and includes at attached tag 50" forming a first indicator FI. Thus, if the composition 30 changes color to sufficiently match the color of the area FI of the tag 50", the user will be informed that the tested withdrawn fluid contains protein and appropriate action can be taken as described above. On the other hand, if the composition 30 does not change to a color matching area FI, the user will know that no protein was detected. Non-limiting examples include integrally forming the tag 50" with the container 10 or separately providing the tag 50" and attaching the same to the container 10 via, e.g., adhesive bonding or ultrasonic welding.

Figure 16:
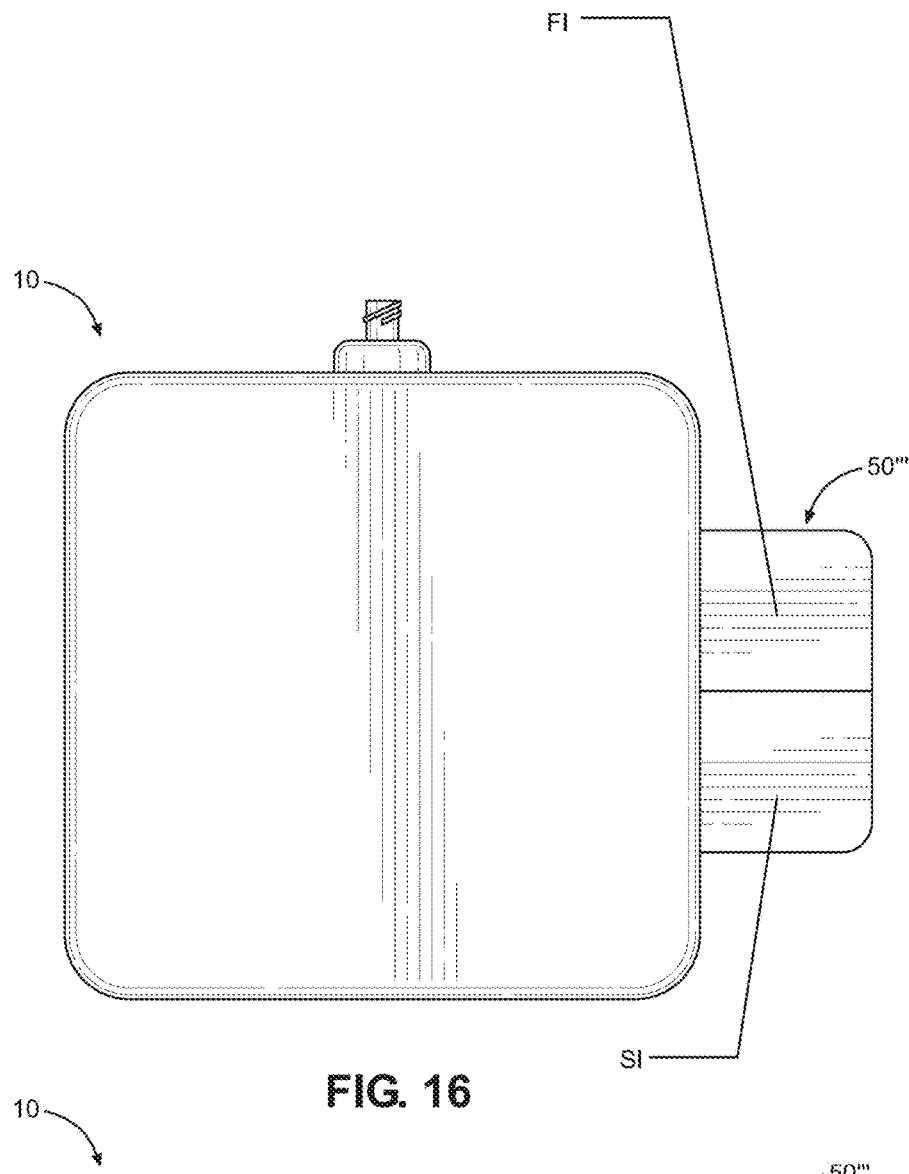
Figure 17:
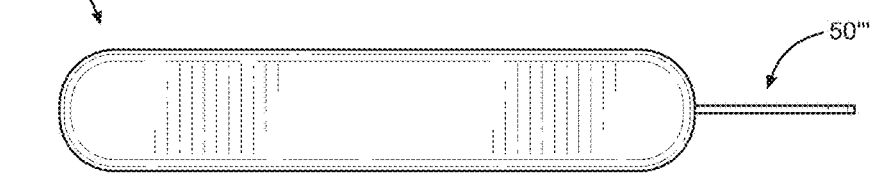

FIGS. 16 and 17 show another embodiment of a container or bag 10 which is sized and configured to contain a predetermined amount of protein-detecting composition 30. In this embodiment, the container 10 is preferably transparent or translucent and includes at attached tag 50''' forming a first indicator FI and a second indicator SI. Thus, if the composition 30 changes color to sufficiently match the color of the area FI of the tag 50''', the user will be informed that the tested withdrawn fluid contains protein and appropriate action can be taken as described above. On the other hand, if the composition 30 does not change to a color matching area FI and has a color sufficiently matching area SI, the user will know that no protein was detected. Non-limiting examples include integrally forming the tag 50''' with the container 10 or separately providing the tag 50'' and attaching the same to the container 10 via, e.g., adhesive bonding or ultrasonic welding.

Alternatively, the embodiment of FIGS. 16 and 17, can utilize a tag 50''' forming a first indicator FI and a second indicator SI wherein if the composition 30 changes color to sufficiently match the color of the area FI of the tag 50''', the user will be informed that the tested withdrawn fluid contains protein and appropriate action can be taken as described above. On the other hand, if the composition 30 changes to a color matching area SI, the user will know that only medicine was detected. Non-limiting examples include integrally forming the tag 50''' with the container 10 or separately providing the tag 50'' and attaching the same to the container 10 via, e.g., adhesive bonding or ultrasonic welding.

In further embodiments, the areas FI, SI and TI can include indicia providing further indication or positive or negative test results such as a plus "+" sign and a minus "−" sign, a check indicator, etc., or other indicators for better or more clearly providing an indication to the user.

Figure 18:
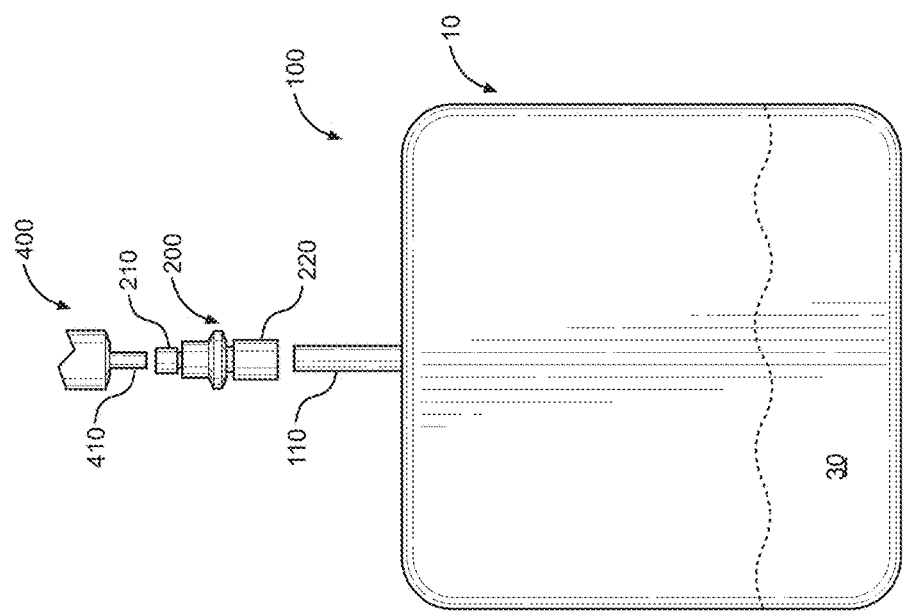

As shown in FIGS. 18 and 19, the invention can also utilize an exemplary container or bag 100 which is sized and configured to contain a predetermined amount of protein-detecting composition 30. In accordance with non-limiting aspects of the invention, this composition 30 is a liquid biuret solution which changes color when contacted by a fluid containing protein. The container can ideally be a bag 100 that has one or more inlet tubes to which one can connect a one-way valve 200. The valve 200 has an inlet side that can be connected to a non-needle injection device 400 and allows for fluid movement only in one direction so that a use can inject fluid into the bag 100 when the valve 200 is used but cannot accidentally withdraw fluid from the bag 100 back into the injection device 400. As in previous embodiments, the bag 100 can have a portion (e.g., a window area) or all, or nearly all, of the bag 100 can be transparent or translucent in order that a color change can be detected from outside the container. Non-limiting exemplary volumes for the bag 10 include from about 15 ml (milliliters) to 100 ml or more. Non-limiting exemplary volumes for the composition 30 include from about a few ml to 30 ml or more with 5 ml being appropriate. The volume of the bag 100 can also be determined in the range of, e.g., about 3 to 4 times, that of the volume of composition 30 contained therein.

In the exemplary embodiment of FIGS. 18 and 19, the valve 200 is separate from the injection device 400 and bag 100 and includes a non-luer-lock type inlet end or connector 210 which can be connected to a non-luer-lock type connector 410 of the injection device 400. The valve 200 also includes an outlet end 220 which can be connected to the tube 110 of the bag 100. Although not shown, it may be desirable to make the connection between the interface 220 and the tube 110 non-removable. This can prevent the user from reusing the bag 100 a second time and also prevent the contents of the bag 100 from spilling out after use. The operation of the system shown in FIGS. 18 and 19 can otherwise take place in a manner similar to that of the other embodiments described above.

Figure 22:
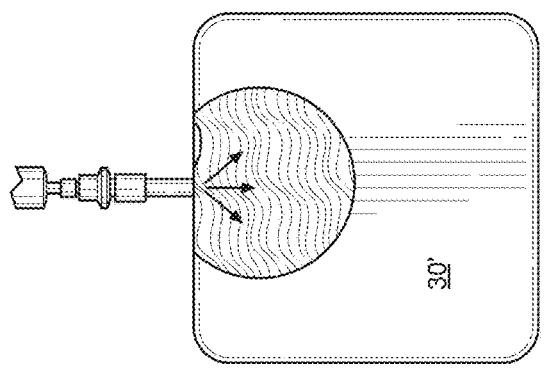
FIG. 22 shows what can happen when the injected withdrawn fluid contacts the coating—with the shaded area representing a reaction zone whereby the coating exhibits a color change.
Figure 21:
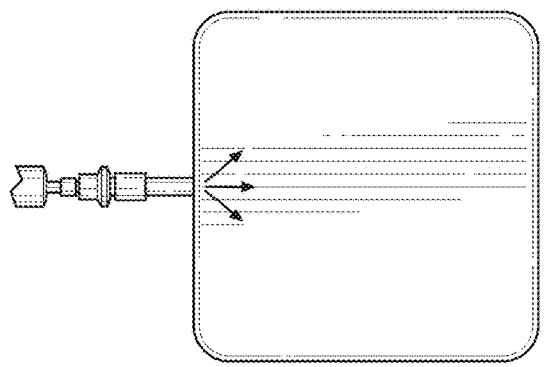
FIG. 21 shows the injection device connected to the one-way valve which in turn is connected to the container or bag and injecting the withdrawn fluid into the container or bag so that it can contact the protein-detecting composition, which in this embodiment has the form of a coating disposed on inner surfaces of the container or bag.

As shown in FIGS. 20-22, the invention can also utilize an exemplary container or bag 100' which is sized and configured to contain a predetermined amount of protein-detecting composition 30'. In accordance with non-limiting aspects of the invention, this composition 30' is a coating of biuret solution which is coated on inside surfaces of the bag 100' and which changes color when contacted by a fluid containing protein. The operation of the system shown in FIGS. 20-22 can otherwise take place in a manner similar to that of the other embodiments described above except that when a coating is used, the area or zone of the coating that is contacted by the injected fluid will be more visually apparent, as shown in FIG. 22.

As shown in FIG. 23, the invention can also utilize an exemplary container or bag 100'' which is sized and configured to contain a predetermined amount of protein-detecting composition (not shown). In accordance with non-limiting aspects of the invention, this composition can be either a liquid or a coating of biuret solution which is coated on inside surfaces of the bag 100'' and which changes color when contacted by a fluid containing protein. The operation of the system shown in FIG. 23 can take place as follows. A user uses a needle type injection device 40' to extract the withdrawn fluid and then injects the needle N into a portion 110'' of the container or bag 100''. If the injected fluid contains protein, this will be indicated by a color change in the protein-detecting composition as in other embodiments described herein. However, unlike other embodiments described herein, no valve is needed in this embodiment as the injection device can be directly injected into the container or bag containing the protein-detecting composition. Variations of this embodiment include injecting the withdrawn fluid into and through a pierceable sidewall of the container or bag 100'' or through a dedicated pierceable member arranged on the container 100''. This embodiment can also utilize a tag or other visual indicator devices such as those used in the embodiments shown in FIGS. 10-16.

As shown in FIG. 24, the invention can also utilize an exemplary bottle or vial 100''' which is sized and configured to contain a predetermined amount of protein-detecting composition (not shown). In accordance with non-limiting aspects of the invention, this composition can be either a liquid or a coating of biuret solution which is coated on inside surfaces of the bottle or vial 100''' and which changes color when contacted by a fluid containing protein. The operation of the system shown in FIG. 24 can take place like the previous embodiment as follows. A user uses a needle type injection device 40' to extract the withdrawn fluid and then injects the needle N into a cap 110''' of the bottle or vial 100'''. If the injected fluid contains protein, this will be indicated by a color change in the protein-detecting composition as in other embodiments described herein. Again, unlike other embodiments described herein, no valve is needed in this embodiment as the injection device can be directly injected into the container or bag containing the protein-detecting composition. This embodiment can also utilize a tag $50^{IV}$ or other visual indicator devices such as those used in the embodiments shown in FIGS. 10-16. In a non-limiting alternative to this embodiment, the vial can be an ampule such as a synthetic resin ampule. This ampule can be either sterilized or non-sterilized.

Figure 25:
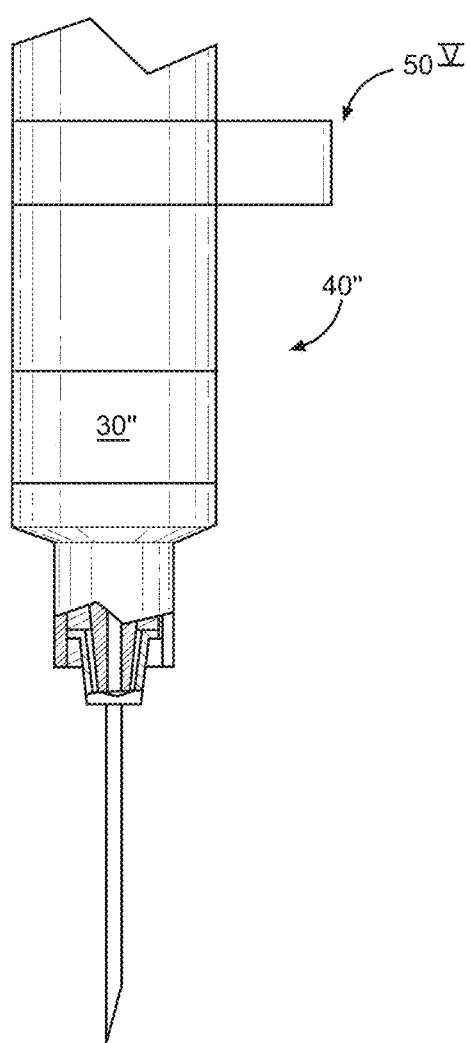
FIG. 25 shows an injection device using a needle that can receive therein the withdrawn fluid. The injection device contains therein a protein detecting composition that can change color when contacted by protein.

As shown in FIG. 25, the invention can also utilize an exemplary injection device 40" which is sized and configured to contain a predetermined amount of protein-detecting composition 30". In accordance with non-limiting aspects of the invention, this composition can be a powder, a liquid or a coating of biuret solution which is coated on an inside surface and which changes color when contacted by a fluid containing protein. The operation of the system shown in FIG. 25 can take place as follows. A user uses a needle type injection device 40" to extract the withdrawn fluid. If the injected fluid contains protein, this will be indicated by a color change in the protein-detecting composition as in other embodiments described herein. This embodiment can also utilize a tag 50$^V$ or other visual indicator devices such as those used in the embodiments shown in FIGS. 10-16.

Figure 26:
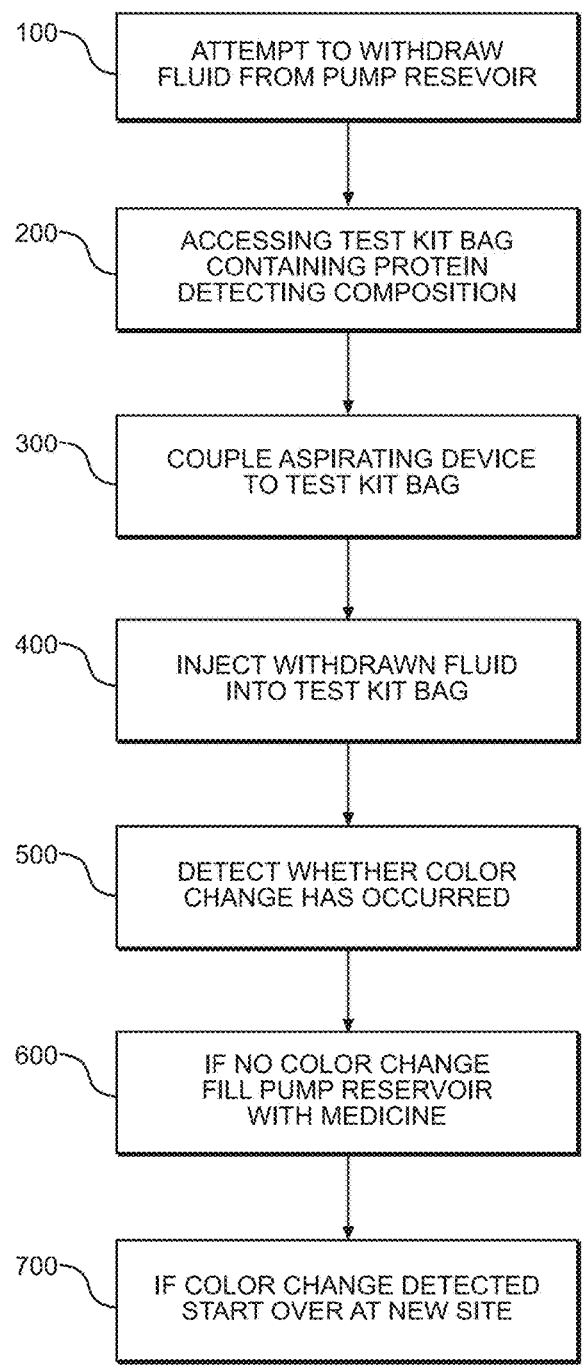
FIG. 26 is a flow chart describing an exemplary method in accordance with the invention.

With reference to FIG. 26, there is shown on non-limiting way in which one can implement a method in accordance with the invention. In stage 100, a user attempts to withdrawn fluid from the implanted pump. This typically occurs with the use injecting a needle into an area of skin overlying the implanted pump and then withdrawing the fluid using a syringe connected to the needle. This can occurs in the manner described with respect to FIGS. 27 and 28.

In stage 200, a user accesses a test kit having a container 10 similar to that shown in FIGS. 1-22.

In stages 300 and 400, a user connects the syringe containing the withdrawn fluid to the container 10 and injects the withdrawn fluid similar to that shown in FIGS. 4 and 5.

In stages 500-700, a user visually detects whether the composition 30 experiences a color change and takes action consistent therewith such as performing a refilling procedure as in stage 600 or starting over in stage 700.

Non-Limiting Examples of Protein-Detecting Composition

Protein-sensing dyes (Biuret test for example) were developed and have been used to identify a number of protein-related disorders and are commonly used to identify protein in urine. Some tests have become complex and are sensitive to certain types of protein, others provide more general recognition of the presence of protein. Protein-detecting compositions generally produce a visually observable reaction on reacting with protein. Examples include, but are not limited to, the Bradford protein assay, which is based on Coomassie Brilliant Blue G-250, and the use of which results in an observable color shift. Preferably, the composition includes a Biuret solution.

Biuret protein test is a well-established test to qualitatively detect this presence of proteins. It generally includes a reagent made up of potassium iodide, potassium sodium tartrate, copper sulfate, and sodium hydroxide. It is based on the cupric ions in the alkaline solution reacting with the peptide bonds of the protein and polypeptides to produce a violet colored complex.

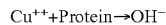  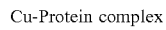

$Cu^{++}$+Protein→$OH^-$    Cu-Protein complex

Numerous examples of protein-sensing dyes and tests are known in the art, and are not set forth herein for the sake of brevity. However, the inventors do not believe the choice of dye or test is a limiting aspect of the invention, as any type could be used according to the invention. Particular types of biuret reaction tests are described, for example, by Gornall et al., in The Journal of Biological Chemistry, Vol. 177, pages 751-766, Feb. 1, 1949, and Weichselbaum, in American Journal of Clinical Pathology, Vol. 10, pages 40-49, March 1946, the entire disclosures of both of which are incorporated by reference herein. Commercially available products are also available. There are various advantages and disadvantages to different tests, relating for example, to the speed and sensitivity of the reaction, and color of the reaction product, but the choice of particular test method is not critical.

The invention contemplates various protein-detecting compositions which can change color upon contact with protein. This includes a change from clear or light blue to violet as well as other changes. Although acceptable results can be obtained when a certain volume or amount of withdrawn fluid is placed into contact with a certain volume or amount of the protein-detecting composition and ratio ranges of between 1 to 1 (withdrawn fluid to protein-changing composition) and 1 to 2 (withdrawn fluid to protein-changing composition) can provide acceptable results, the invention contemplates other ratio ranges. In addition, the invention can be implemented with a certain or threshold amount of withdrawn fluid such as 1 milliliter and with a predetermined range or amount of protein-detecting composition such as between 2 and 6 milliliters. A preferred embodiment of the present invention includes the use of at least 4 milliliters, with 4 milliliters of withdrawn fluid mixed therewith.

The protein-detecting compositions used in the present invention may be in dry form such as powder form or in liquid form. For example, in dry form, the separate dry elements of the reaction mixture can be included, and then rely on the liquid from the biological fluid to dissolve the elements for the reaction to occur. Alternatively, for example, a liquid composition may be dried (after dissolving the various components in a solvent), and the dried composition may be mixed and re-dissolved in biological fluid. Or the protein-detecting composition may be in liquid form, which can be mixed with the biological fluid to be tested for protein. Various combinations and modifications will be readily apparent to skilled persons after reviewing the present specification.

Note that the protein-detecting compositions are intended to provide a basis for determining whether a composition includes a sufficient amount of protein to be a cause for concern. The inventors of course recognize the any injection into human tissue will almost necessarily introduce some protein into or onto a needle tip, which can be detected by the protein-detecting compositions. Thus, the inventors contemplate that some protein in a sample may be unavoidable, and contemplate that a threshold color change may determined through a standard concentration curve to determine what level of protein is considered to be a cause for concern. While not wishing to be bound to any particular concentration, a concentration of protein of about 30 mg/ml or higher in the withdrawn fluid will generally be considered as evidence that the needle has been inserted into human fluid, i.e., outside the pump reservoir.

The inventors certainly also recognize that certain human conditions might result in a normally higher or lower concentration of protein in serum. For example, liver disease, acute infection, or immunodeficiency can result in low serum albumin concentration; and other diseases such as paraproteinemia (caused by certain leukemias and lymphomas), Hodgkin's lymphoma, and leukemia can result in an increase in immunoglobulins. The presence of such conditions can be taken into account by the practitioner in determining whether a color change in the protein-detecting test should be considered cause for concern.

EXAMPLES

Development of a qualitative colour test for proteins in abdominal body fluid.

Sensitivity to be reached 0.03 g/mL=30 mg/mL.

The value of 30 mg/ml was determined as the target value based on reported levels of total protein in peritoneal fluid (normally exudate material is >3.0 g/dl with transudate <3.0 g/dl).

Objectives:
(1) Develop formulation for peritoneal fluid
(2) Define appropriate Biuret solution to protein fluid ratio
(3) Define protein operating range and limit of detection for the Biuret solution
(5) Verify stability of the solution
(6) Use of control samples with the Biuret solutions Technical Summary (1) Biuret Reagent Development Three different Biuret solutions were tested—with all solutions sensitive enough to visualize 30 mg/mL of protein. Gornall and Weichselbaum refer to the sources of biuret found in a literature search.

(1.1) Biuret Formulations
Gornall biuret solution. See FIG. 29.
Weichselbaum biuret solution. See FIG. 30.
Modified biuret test solution. See FIG. 31.

(1.2) Formulation Performance

For this the various Biuret solutions above were evaluated against visual colour and spectrophotometrically.

Figure 33:
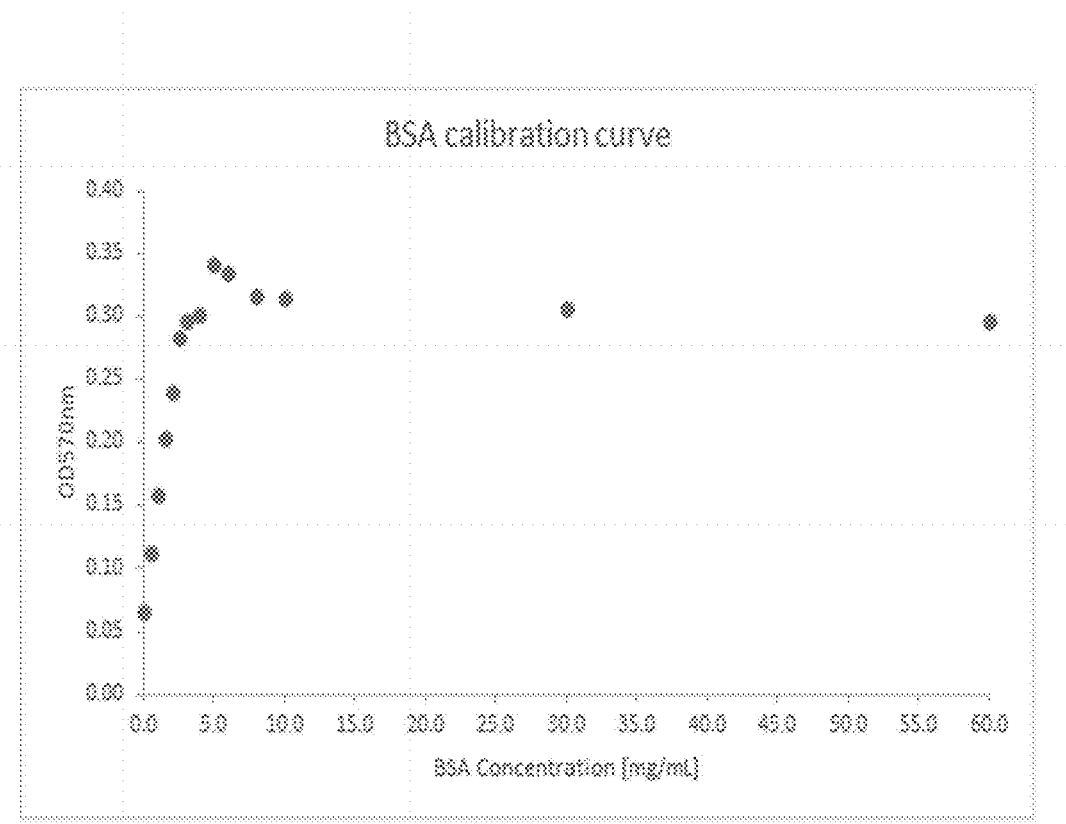
FIG. 33 is a graph illustrating a BSA calibration curve.

Gornall. See FIGS. 32 and 33.

Conclusion: The BSA calibration curve is linear until about 2.5 mg/ml. For this reason, only the 0-2.5 mg/ml curve was used to calculate concentrations. The total protein concentration found is 77 mg/ml (120% recovery). The target concentration of 30 mg/ml is clearly visible.

The Weichselbaum solution performance was compared again against the Gornall See FIGS. 34-36.

Conclusion: The Weichselbaum Biuret solution reaches a higher OD value than the Gornall solution. Also the Weichselbaum signal develops in time more than the Gornall signal.

Solution

The solution performance was tested and compared against the two previous solution types. See FIGS. 37 and 38.

Conclusion: the biuret solution results in a good performance. A very low background and good colour intensity @(10 mg/ml, OD 0.710).

(2) Evaluation of the performance of different ratios of biuret reagent solutions with BSA calibrators in different protein:biuret ratios: 1:3, 1:2, 1:1, 2:1, 3:1. See FIGS. 39-42.

Conclusion: There is a wide range of color changing ratios versus the typically specified 1:1 preferred biuret ratio. This allows for a single volume of biuret fill with a range of potential pump aspiration volumes and still provide valid results (3) Protein Operating Range and Limit of Detection Determination (3.1) From the above section 1.2 an operational range of 1.0 to 10.0 mg/ml was established for all Biuret solutions. However, the % CV was best for the solution with a relatively low background and hence less variability.

Further linearity studies were carried out listed below these confirmed the linear range. See FIGS. 43-45.

Conclusion: Linearity and hence range was demonstrated from 1.0 mg/ml to 10.0 mg/mi. LOD of 0.1 mg/ml was determined.

(3.2) Also a visual study was conducted with laboratory personnel to determine when an end point (color change) could be visually detected and to see what concentration of protein this corresponded to. The spectrophotometric method was used a reference.

Conclusion (without showing all data): At the concentration of 1 mg/ml, all laboratory personnel (n=6) could visually detect the colour change.

(4) Stability

Stability was initially carried out on Gornall and Weichelbaum solutions. After this initial study and evaluation, the Weichelbaum reagent was not as stable and further stability was not continued for this solution.

Stability studies were carried out on the solutions at various conditions.

Conclusion (data not shown): The solutions all demonstrate acceptable stability.

(5) Control Samples (Including Drug)

(5.1) Baclofen as a Negative Control

Lioresal (baclofen (2.0 mg/ml)) was used as a negative control to determine if the use influenced a false positive result. See FIG. 46.

Conclusion: Baclofen solution alone (ie. Aspirate in a real world setting) does not create a color change and therefore a false-positive.

Conclusion from all examples:

Each of the various biuret solutions exhibited acceptable performance.

What is claimed:

1. A method of safely refilling an implanted infusion pump, the method comprising:
   locating a reservoir refill septum of the implanted infusion pump;
   preventing inadvertent injection into an area overlying the implanted infusion pump; and
   filling or refilling the implanted infusion pump,
   wherein the preventing comprises:
      withdrawing fluid from said area while attempting to fill or refill a reservoir of the implanted infusion pump; and
      after the withdrawing, contacting the fluid with a protein-detecting composition to determine whether the protein-detecting composition experiences a reaction.

2. The method of claim 1, wherein the method further comprises:
   accessing a container containing the protein-detecting composition;
   injecting the withdrawn fluid into the container;
   determining whether or not the protein-detecting composition experiences a color change.

3. The method of claim 2, wherein the method further comprises:
   filling or refilling the implanted infusion pump only after the determining.

* * * * *